US010147236B2

(12) United States Patent
Grossman et al.

(10) Patent No.: US 10,147,236 B2
(45) Date of Patent: Dec. 4, 2018

(54) SMART TOOLS AND WORKSPACES FOR DO-IT-YOURSELF TASKS

(71) Applicant: AUTODESK, Inc., San Rafael, CA (US)

(72) Inventors: Tovi Grossman, Toronto (CA); George Fitzmaurice, Toronto (CA); Jarrod Knibbe, Bristol (GB)

(73) Assignee: AUTODESK, INC., San Rafael, CA (US)

( * ) Notice: Subject to any disclaimer, the term of this patent is extended or adjusted under 35 U.S.C. 154(b) by 0 days.

(21) Appl. No.: 14/968,738

(22) Filed: Dec. 14, 2015

(65) Prior Publication Data

US 2016/0171845 A1 Jun. 16, 2016

Related U.S. Application Data

(60) Provisional application No. 62/092,208, filed on Dec. 15, 2014.

(51) Int. Cl.
| G08B 13/14 | (2006.01) |
| G06T 19/00 | (2011.01) |
| B25H 3/00 | (2006.01) |
| G08B 5/36 | (2006.01) |
| G08B 21/02 | (2006.01) |

(Continued)

(52) U.S. Cl.
CPC .............. *G06T 19/006* (2013.01); *B25H 3/00* (2013.01); *F16P 3/147* (2013.01); *G02B 27/017* (2013.01); *G06Q 10/06* (2013.01); *G08B 5/36* (2013.01); *G08B 21/02* (2013.01); *G08B 21/24* (2013.01); *G09B 19/003* (2013.01); *G09B 19/24* (2013.01); *A61F 9/029* (2013.01); *G02B 2027/0178* (2013.01)

(58) Field of Classification Search
None
See application file for complete search history.

(56) References Cited

U.S. PATENT DOCUMENTS

| 5,315,289 A | 5/1994 | Fuller et al. |
| 5,796,341 A | 8/1998 | Stratiotis |

(Continued)

OTHER PUBLICATIONS

Chi, P.-Y., Ahn, S., Ren, A., et al. "MixT: Automatic Generation of Step-by-step Mixed Media Tutorials". UIST '12, 93-102.

(Continued)

*Primary Examiner* — Thomas McCormack
(74) *Attorney, Agent, or Firm* — Artegis Law Group, LLP

(57) ABSTRACT

One embodiment of the invention disclosed herein provides techniques for assisting with performing a task within a smart workspace environment. A smart workspace system includes a memory that includes a workspace management application. The smart workspace system further includes a processor that is coupled to the memory and, upon executing the workspace management application, is configured to perform various steps. The processor detects that a first step included in a plurality of steps associated with a task is being performed. The processor displays one or more information panels associated with performing the current step. The processor further communicates with augmented safety glasses, augmented tools, and an augmented toolkit to safely and efficiently through a series of steps to complete the task.

20 Claims, 12 Drawing Sheets

(51) Int. Cl.
| | |
|---|---|
| G08B 21/24 | (2006.01) |
| G02B 27/01 | (2006.01) |
| G09B 19/00 | (2006.01) |
| F16P 3/14 | (2006.01) |
| G06Q 10/06 | (2012.01) |
| G09B 19/24 | (2006.01) |
| A61F 9/02 | (2006.01) |

(56) References Cited

U.S. PATENT DOCUMENTS

| | | | |
|---|---|---|---|
| 6,119,681 | A | 9/2000 | Lilke |
| 7,336,174 | B1* | 2/2008 | Maloney .......... G08B 13/1427 340/568.1 |
| 8,081,262 | B1 | 12/2011 | Perez |
| 8,208,681 | B2 | 6/2012 | Heller |
| 2003/0089696 | A1 | 5/2003 | Yokoyama et al. |
| 2004/0100384 | A1 | 5/2004 | Chen |
| 2007/0215700 | A1* | 9/2007 | Reznik .............. H01Q 1/2216 235/385 |
| 2008/0062338 | A1 | 3/2008 | Herzog |
| 2008/0088454 | A1* | 4/2008 | Flores .................. B25H 3/00 340/572.4 |
| 2009/0072631 | A1 | 3/2009 | Iida et al. |
| 2010/0252626 | A1* | 10/2010 | Elizondo ............ G06Q 10/087 235/385 |
| 2011/0120738 | A1 | 5/2011 | Miwa et al. |
| 2011/0136552 | A1 | 6/2011 | Lee |
| 2012/0257175 | A1 | 10/2012 | Shi et al. |
| 2012/0326837 | A1 | 12/2012 | Ajay |
| 2013/0076898 | A1* | 3/2013 | Philippe .............. H04N 7/18 348/143 |
| 2013/0109375 | A1 | 5/2013 | Zeiler et al. |
| 2013/0257622 | A1 | 10/2013 | Davalos |
| 2014/0204331 | A1 | 7/2014 | Huh |
| 2014/0273847 | A1 | 9/2014 | Nixon |
| 2014/0327528 | A1 | 11/2014 | Matsumoto |
| 2015/0153906 | A1* | 6/2015 | Liao .................. G06F 17/3079 715/709 |
| 2015/0248826 | A1 | 9/2015 | Hahn |
| 2015/0273610 | A1 | 10/2015 | Denis et al. |
| 2016/0171772 | A1 | 6/2016 | Ryznar et al. |
| 2016/0307459 | A1 | 10/2016 | Chestnut et al. |

OTHER PUBLICATIONS

Chi, P.-Y., Liu, J., Linder, J., et al. "DemoCut: Generating Concise Instructional Videos for Physical Demonstrations". UIST '13, 141-150.

Fernquist, J., Grossman, T. and Fitzmaurice, G. "SketchSketch Revolution: An Engaging Tutorial System for Guided Sketching and Application Learning". UIST '11, 373-382.

Grabler, F., Agrawala, M., Li, W., Dontcheva, M. and Igarashi, T. "Generating Photo Manipulation Tutorials by Demonstration". SIGGRAPH '09, 66:1-66:9.

Grossman, T. and Fitzmaurice, G. "ToolClips: An Investigation of Contextual Video Assistance for Functionality Understanding". CHI '10, 1515-1524.

Grossman, T., Matejka, J. and Fitzmaurice, G. "Chronicle: Capture, Exploration, and Playback of Document Workflow Histories". UIST '10, 143-152.

Henderson, S.J. and Feiner, S.K. "Augmented Reality in the Psychomotor Phase of a Procedural Task". ISMAR '11, 191-200.

Ju, W., Bonanni, L., Fletcher, R., et al., "Origami Desk: Integrating Technological Innovation and Human-centric Design". DIS '02, 399-405.

Kelleher, C. and Pausch, R. "Stencils-based Tutorials: Design and Evaluation". CHI '05, 541-550.

Kong, N., Grossman, T., Hartmann, B., Agrawala, M. and Fitzmaurice, G. "Delta: A Tool for Representing and Comparing Workflows". CHI '12, 1027-1036.

Lafreniere, B., Grossman, T. and Fitzmaurice, G. "Community Enhanced Tutorials: Improving Tutorials with Multiple Demonstrations". CHI '13, 1779-1788.

Makerspace Team, et. Makerspace Playback. 2013. http://makerspace.com/wp-content/uploads/2013/02/ MakerspacePlaybook-Feb2013.pdf.

Reiners, D., Stricker, D., Klinker, G. and Müller, S. "Augmented Reality for Construction Tasks: Doorlock Assembly". 31-46.

Tanenbaum, J.G., Williams, A.M., Desjardins, A. and Tanenbaum, K. "Democratizing Technology: Pleasure, Utility and Expressiveness in DIY and Maker Practice". CHI '13, 2603-2612.

Tang, A., Owen, C., Biocca, F. and Mou, W. "Comparative Effectiveness of Augmented Reality in Object Assembly"CHI '03, 73-80.

Torrey, C., Churchill, E.F. and McDonald, D.W. "Learning How: The Search for Craft Knowledge on the Internet". CHI '09, 1371-1380.

Torrey, C., McDonald, D.W., Schilit, B.N. and Bly, S. "How-To pages: Informal systems of expertise sharing". ECSCW 2007. L.J. Bannon, I. Wagner, C. Gutwin, R.H.R. Harper, and K. Schmidt, eds. Springer London. 391-410.

Instructables—"DIY How to Make Instructions" http://www.instructables.com/.

Make | DIY projects, how-tos, and inspiration from geeks, makers, and hackers. http://makezine.com/.

IKEA Hackers—Clever ideas and hacks for your IKEA. http://www.ikeahackers.net/.

Zoran, A. and Paradiso, J.A. "FreeD: A Freehand Digital Sculpting Tool". CHI '13, 2613-2616.

Proximity Box, http://www.instructables.com/id/Depth-sensing-Box/.

Phidgets Inc.—Unique and Easy to Use USB Interfaces. http://.phidgets.com/.

Korn, O., Schmidt, A., and Hörz, T., "The potentials of in-situ-projection for augmented workplaces in production: a study with impaired persons", CHI '13, 979-984.

Rosenthal, S., Kane, S.K., Wobbrock, J.O. and Avrahami, D. "Augmenting On-screen Instructions with Microprojected Guides: When It Works, and when It Fails". UbiComp '10, 203-212.

Wakkary, R., Schilling, M.L., Dalton, M., et al. "Tutorial Authorship and Hybrid Designers: The Joy (and Frustration) of DIY Tutorials". CHI '15, 609-618.

Weichel, C., Alexander, J., Kamik, A. and Gellersen, H. "SPATA: Spatio-Tangible Tools for Fabrication-Aware Design". TEI '15, 189-196.

Office Action for U.S. Appl. No. 14/968,677, dated Nov. 10, 2016.
Office Action for U.S. Appl. No. 14/968,704, dated Jun. 27, 2017, 21 pages.
Final Office Action for U.S. Appl. No. 14/968,767, dated Jun. 20, 2018, 16 pages.
Office Action for U.S. Appl. No. 14/968,767, dated Jan. 9, 2018, 15 pages.
Office Action for U.S. Appl. No. 14/968,677, dated Jan. 26, 2018, 13 pages.

\* cited by examiner

SMART TOOLS AND WORKSPACES FOR DO-IT-YOURSELF TASKS

CROSS-REFERENCE TO RELATED APPLICATIONS

This application claims the benefit of U.S. provisional patent application titled, "SMART TOOLS AND WORKSPACES FOR DO-IT-YOURSELF TASKS," filed on Dec. 15, 2014 and having Ser. No. 62/092,208. The subject matter of this related application is hereby incorporated herein by reference.

BACKGROUND OF THE INVENTION

Field of the Invention

The present invention relates generally to computer-based systems and, more specifically, to smart tools and workspaces for do-it-yourself tasks.

Description of the Related Art

Makerspaces, also referred to herein as workspaces, provide a workspace where individuals, commonly referred to as "makers," have access to tools, equipment, raw materials, guidance, and other resources to perform various do-it-yourself (DIY) tasks, complete projects, and, more generally, "make things." In addition to providing a workspace, some makerspaces provide a learning environment for individuals to socialize and collaborate with other makers that share common interests. As an alternative, a maker may have a makerspace in his or her home, where the maker can perform DIY tasks and complete projects. A typical makerspace can accommodate multiple makers at any given time, where the skill level of the makers can range from novices with little to no experience and skill to experts with a high level of experience and skill. Likewise, makers that have a personal makerspaces in the home may have skill levels ranging from novice to expert.

One drawback of makerspace environments is that makers typically work with little to no supervision, whether the work is performed in a public makerspace or in a personal makerspace at home. In addition, some makerspaces include potentially dangerous equipment that is capable of causing injury, particularly when the equipment is used improperly or without the proper safety equipment. Further, many makers do not know how to perform particular tasks, how to select the proper equipment to complete the task, how to select the appropriate materials, or how to locate the needed tools and materials. As a result, makers oftentimes can become frustrated, or worse, may cause injury to themselves or others.

As the foregoing illustrates, what is needed are more effective ways for makers to perform tasks.

SUMMARY OF THE INVENTION

One embodiment of the invention disclosed herein provides techniques for assisting with performing a task within a smart workspace environment. A smart workspace system includes a memory that includes a workspace management application. The smart workspace system further includes a processor that is coupled to the memory and, upon executing the workspace management application, is configured to perform various steps. The processor detects that a first step included in a plurality of steps associated with a task is being performed. The processor displays one or more information panels associated with performing the current step. The processor further communicates with augmented safety glasses, augmented tools, and an augmented toolkit to safely and efficiently through a series of steps to complete the task.

Other embodiments include, without limitation, a computer-readable medium that includes instructions that enable a processing unit to implement one or more aspects of the disclosed methods. Other embodiments include, without limitation, a subsystem that includes a processing unit configured to implement one or more aspects of the disclosed methods as well as a computing system configured to implement one or more aspects of the disclosed methods.

At least one advantage of the disclosed techniques is that makers in a public or private makerspace perform steps in a given task safely and efficiently. Makers are reminded to properly use tools and wear safety glasses and are prevented from using tools in a dangerous manner, improving safety and reducing liability in makerspace environments.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the present invention. However, it will be apparent to one of skill in the art that embodiments of the present invention may be practiced without one or more of these specific details.

Among other things, embodiments of the present invention are directed towards a computer network that can be implemented to manage and process all of the sensor-related data as well as generate and provide relevant information to users based on the collected data. Other embodiments are directed towards a "smart" makerspace that provides, among other things, a digital workbench, augmented safety glasses, instrumented power-tools, an augmented toolkit, and environmentally aware audio. Other embodiments are directed towards "smart" safety glasses that can detect when they are being worn by a user. That information, for example, can be associated with different tools and machines and also transmitted to the user to enhance overall workspace safety. Other embodiments are directed towards implementing tools and machines with a variety of sensors that can be used to monitor the use of those machines and tools and to provide time-relevant safety information to users. Embodiments also are directed towards a "smart" toolkit having instrumented bins and configured to inform a user where relevant tools and other toolkit items are located when the user is working on a task or project. The toolkit also can determine when a user takes items out of the toolkit or places items into the toolkit and can track the quantities of the different items stored in the toolkit.

Hardware Overview

Figure 1:
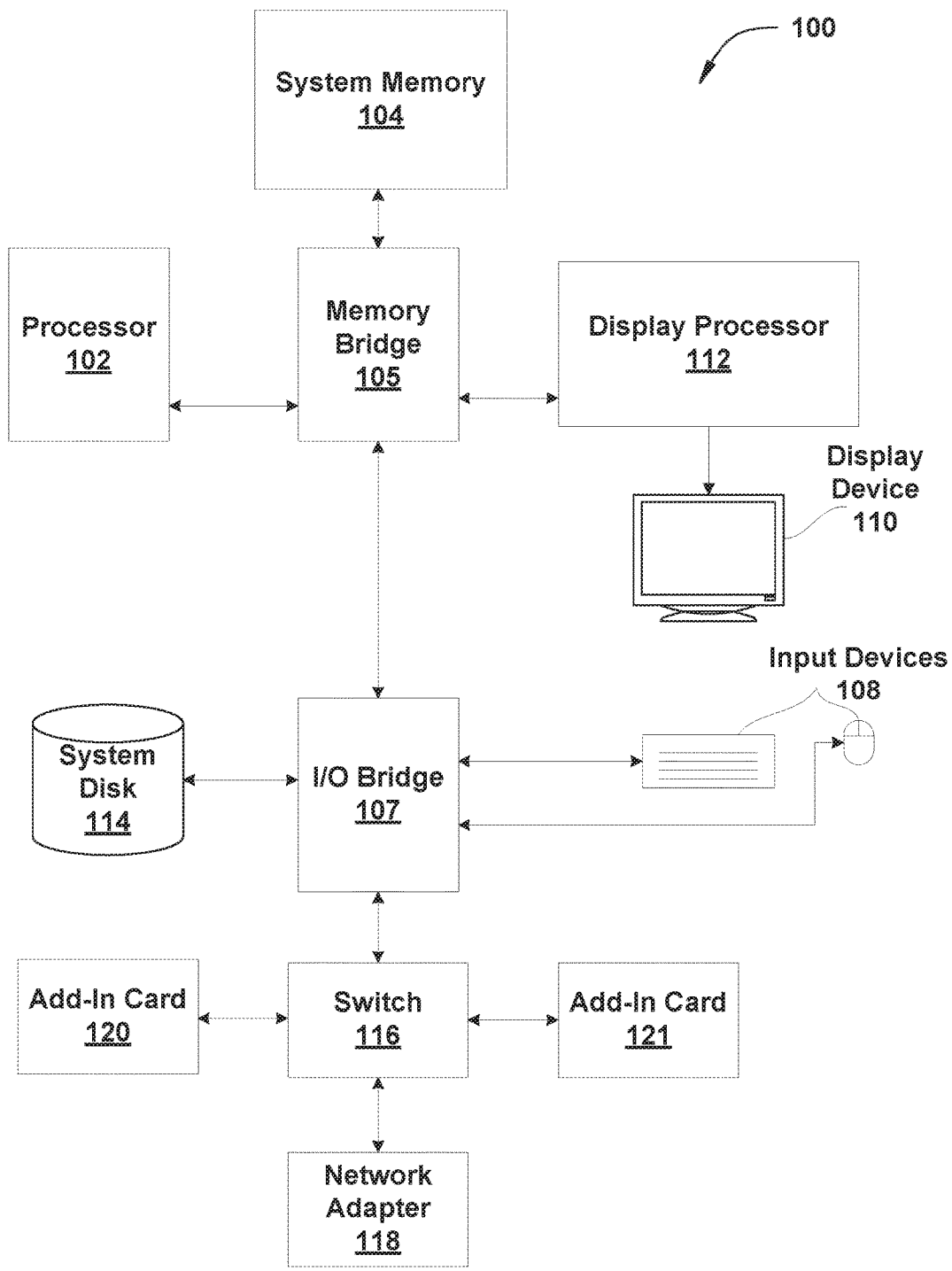
FIG. 1 illustrates a computing system configured to implement one or more aspects of the present invention.

FIG. 1 illustrates a computing system 100 configured to implement one or more aspects of the present invention. This figure in no way limits or is intended to limit the scope of the present invention. Computing system 100 may be a personal computer, video game console, personal digital assistant, mobile phone, mobile device, or any other device suitable for implementing one or more aspects of the present invention.

As shown, computing system 100 includes, without limitation, a processor 102, display processor 112, input/output (I/O) bridge 107, and system memory 104, coupled together and communicating via a bus path that may include a memory bridge 105. Processor 102 may be any technically feasible form of processing device configured to process data and execute program code. Processor 102 could be, for example, a central processing unit (CPU), a graphics processing unit (GPU), an application-specific integrated circuit (ASIC), a field-programmable gate array (FPGA), and so forth. Likewise, display processor 112 may be any technically feasible form of processing device configured to process data and execute program code. Display processor 112 could be, for example, a central processing unit (CPU), a graphics processing unit (GPU), an application-specific integrated circuit (ASIC), a field-programmable gate array (FPGA), and so forth.

Processor 102 and display processor 112 include one or more processing cores. In operation, one or both of processor 102 and display processor 112 is the master processor of computing system 100, controlling and coordinating operations of other system components. System memory 104 stores software applications and data for use by processor 102. Either or both of processor 102 and display processor 112 execute software applications stored within system memory 104 and optionally an operating system. In particular, either or both of processor 102 and display processor 112 executes software and then performs one or more of the functions and operations set forth in the present application. Memory bridge 105, which may be, e.g., a Northbridge chip, is connected via a bus or other communication path (e.g., a HyperTransport link) to an I/O (input/output) bridge 107. I/O bridge 107, which may be, e.g., a Southbridge chip, receives user input from one or more user input devices 108 (e.g., keyboard, mouse, joystick, digitizer tablets, touch pads, touch screens, still or video cameras, motion sensors, and/or microphones) and forwards the input to processor 102 via memory bridge 105.

Display processor 112 is coupled to memory bridge 105 via a bus or other communication path (e.g., a PCI Express, Accelerated Graphics Port, or HyperTransport link); in one embodiment display processor 112 is a graphics subsystem that includes at least one graphics processing unit (GPU) and graphics memory. Graphics memory includes a display memory (e.g., a frame buffer) used for storing pixel data for each pixel of an output image. Graphics memory can be integrated in the same device as the GPU, connected as a separate device with the GPU, and/or implemented within system memory 104.

Display processor 112 periodically delivers pixels to a display device 110 (e.g., a screen or conventional CRT, plasma, OLED, SED or LCD based monitor or television). Additionally, display processor 112 may output pixels to film recorders adapted to reproduce computer generated images on photographic film. Display processor 112 can provide display device 110 with an analog or digital signal.

A system disk 114 is also connected to I/O bridge 107 and may be configured to store content and applications and data for use by processor 102 and display processor 112. System disk 114 provides non-volatile storage for applications and data and may include fixed or removable hard disk drives, flash memory devices, and CD-ROM, DVD-ROM, Blu-ray, HD-DVD, or other magnetic, optical, or solid state storage devices.

A switch 116 provides connections between I/O bridge 107 and other components such as a network adapter 118 and various add-in cards 120 and 121. Network adapter 118 allows computing system 100 to communicate with other systems via an electronic communications network, and may include wired or wireless communication over local area networks and wide area networks such as the Internet.

Other components (not shown), including USB or other port connections, film recording devices, and the like, may also be connected to I/O bridge 107. For example, an audio processor may be used to generate analog or digital audio output from instructions and/or data provided by processor 102, system memory 104, or system disk 114. Communication paths interconnecting the various components in FIG. 1 may be implemented using any suitable protocols, such as PCI (Peripheral Component Interconnect), PCI Express (PCI-E), AGP (Accelerated Graphics Port), HyperTransport, or any other bus or point-to-point communication protocol (s), and connections between different devices may use different protocols, as is known in the art.

In one embodiment, display processor 112 incorporates circuitry optimized for graphics and video processing, including, for example, video output circuitry, and constitutes a graphics processing unit (GPU). In another embodiment, display processor 112 incorporates circuitry optimized for general purpose processing. In yet another embodiment, display processor 112 may be integrated with one or more other system elements, such as the memory bridge 105, processor 102, and I/O bridge 107 to form a system on chip (SoC). In still further embodiments, display processor 112 is omitted and software executed by processor 102 performs the functions of display processor 112.

Pixel data can be provided to display processor 112 directly from processor 102. In some embodiments of the present invention, instructions and/or data representing a scene are provided to a render farm or a set of server computers, each similar to computing system 100, via network adapter 118 or system disk 114. The render farm generates one or more rendered images of the scene using the provided instructions and/or data. These rendered images may be stored on computer-readable media in a digital format and optionally returned to computing system 100 for display. Similarly, stereo image pairs processed by display processor 112 may be output to other systems for display, stored in system disk 114, or stored on computer-readable media in a digital format.

Alternatively, processor 102 provides display processor 112 with data and/or instructions defining the desired output images, from which display processor 112 generates the pixel data of one or more output images, including characterizing and/or adjusting the offset between stereo image pairs. The data and/or instructions defining the desired output images can be stored in system memory 104 or graphics memory within display processor 112. In an embodiment, display processor 112 includes 3D rendering capabilities for generating pixel data for output images from instructions and data defining the geometry, lighting shading, texturing, motion, and/or camera parameters for a scene. Display processor 112 can further include one or more programmable execution units capable of executing shader programs, tone mapping programs, and the like.

Processor 102, render farm, and/or display processor 112 can employ any surface or volume rendering technique known in the art to generate one or more rendered images from the provided data and instructions, including rasterization, scanline rendering REYES or micropolygon rendering, ray casting, ray tracing, image-based rendering techniques, and/or combinations of these and any other rendering or image processing techniques known in the art.

It will be appreciated that the system shown herein is illustrative and that variations and modifications are possible. The connection topology, including the number and arrangement of bridges, may be modified as desired. For instance, in some embodiments, system memory 104 is connected to processor 102 directly rather than through a bridge, and other devices communicate with system memory 104 via memory bridge 105 and processor 102. In other alternative topologies display processor 112 is connected to I/O bridge 107 or directly to processor 102, rather than to memory bridge 105. In still other embodiments, I/O bridge 107 and memory bridge 105 might be integrated into a single chip. The particular components shown herein are optional; for instance, any number of add-in cards or peripheral devices might be supported. In some embodiments, switch 116 is eliminated, and network adapter 118 and add-in cards 120, 121 connect directly to I/O bridge 107.

Smart Tools and Workspaces for DIY Tasks

Figure 2:
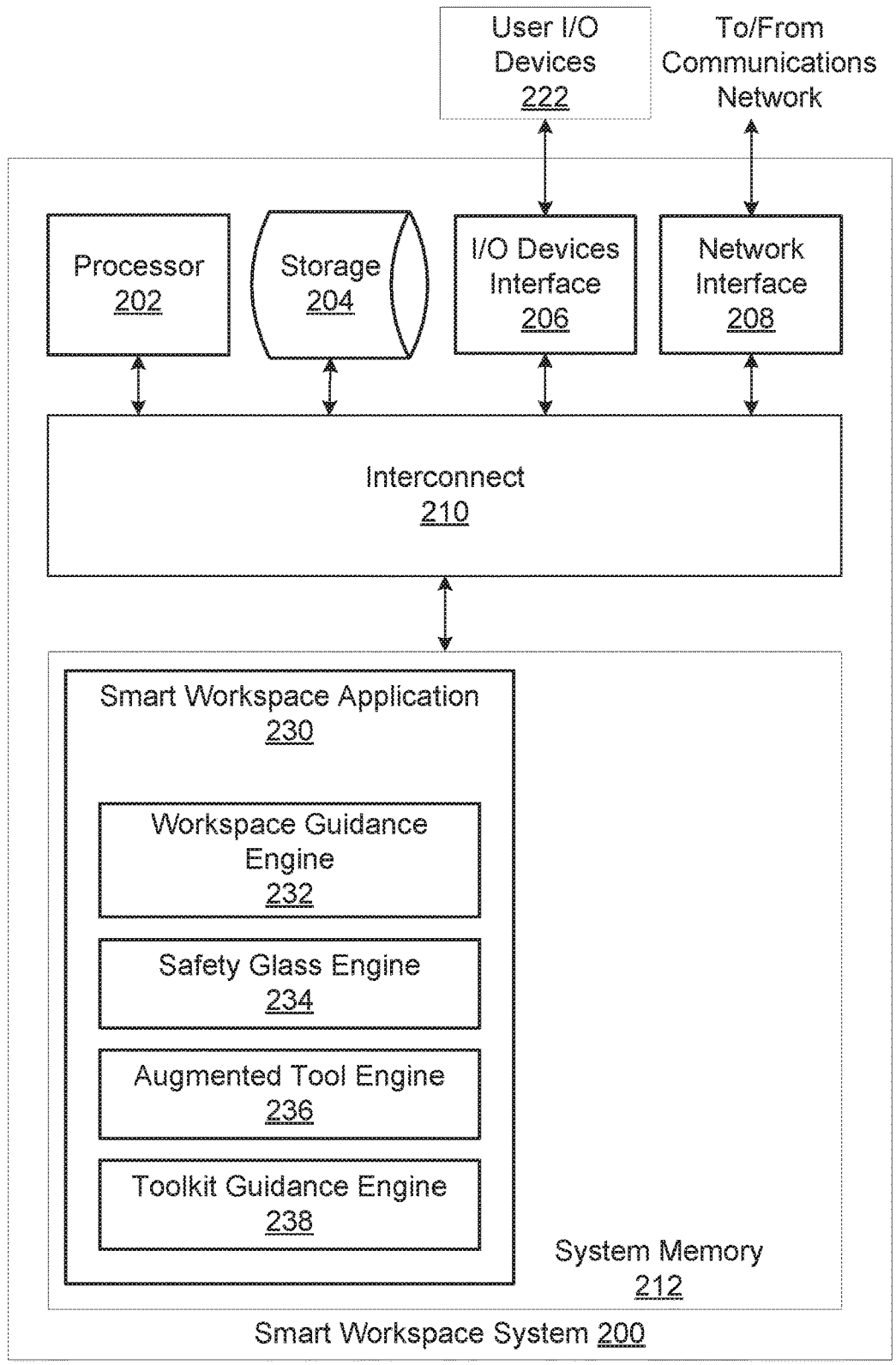
FIG. 2 is a block diagram of a smart workspace system, according to various embodiments of the present invention.

FIG. 2 is a block diagram of a smart workspace system 200, according to various embodiments of the present invention. In some embodiments, at least a portion of the smart workspace system 200 may be implemented via the computing system 100 of FIG. 1. As shown, the smart workspace system 200 includes, without limitation, a central processing unit (CPU) 202, storage 204, an input/output (I/O) devices interface 206, a network interface 208, an interconnect 210, and a system memory 212. The computing system 100 of FIG. 1 can be configured to implement the smart workspace system 200. The processor 202, storage 204, I/O devices interface 206, network interface 208, interconnect 210, and system memory 212 function substantially the same as described in conjunction with FIG. 1 except as further described below.

The processor 202 retrieves and executes programming instructions stored in the system memory 212. Similarly, the processor 202 stores and retrieves application data residing in the system memory 212. The interconnect 210 facilitates transmission, such as of programming instructions and application data, between the processor 202, input/output (I/O) devices interface 206, storage 204, network interface 208, and system memory 212. The I/O devices interface 206 is configured to receive input data from user I/O devices 222. Examples of user I/O devices 222 may include one of more buttons, a keyboard, and a mouse or other pointing device. The I/O devices interface 206 may also include an audio output unit configured to generate an electrical audio output signal, and user I/O devices 222 may further includes a speaker configured to generate an acoustic output in response to the electrical audio output signal. Another example of a user I/O device 222 is a display device that generally represents any technically feasible means for generating an image for display. For example, the display device could be a liquid crystal display (LCD) display, CRT display, or DLP display. The display device may be a TV that includes a broadcast or cable tuner for receiving digital or analog television signals.

Processor 202 is included to be representative of a single CPU, multiple CPUs, a single CPU having multiple processing cores, and the like. And the system memory 212 is generally included to be representative of a random access memory. The storage 204 may be a disk drive storage device. Although shown as a single unit, the storage 204 may be a combination of fixed and/or removable storage devices, such as fixed disc drives, floppy disc drives, tape drives, removable memory cards, or optical storage, network attached storage (NAS), or a storage area-network (SAN). Processor 202 communicates to other computing devices and systems via network interface 208, where network interface 208 is configured to transmit and receive data via a communications network.

The system memory 212 includes, without limitation, a smart workspace application 230 that further includes a workspace guidance engine 232, a safety glass engine 234, an augmented tool engine 236, and a toolkit guidance engine 238.

The workspace guidance engine 232 provides a context-rich, immersive instructional workspace for novice and intermediate makers. The workspace guidance engine 232 guides makers through the completion of a DIY task, while providing detailed contextually-relevant assistance, domain knowledge, tool location, usage cues, and safety advice. The workspace guidance engine 232 drives a digital workbench to guide the maker via various user interface panels of information that include, without limitation, the steps needed to complete a task, detailed description of the current step, tools and materials needed to perform the current step, and whether safety glasses are needed to perform the current step. The workspace guidance engine 232 presents the user interface panels to the user via any technically feasible technique, including, without limitation, displaying the user interface panels on a horizontally or vertically mounted display surface, projecting the user interface panels onto a horizontal or vertical surface, and displaying the user interface panels on a mobile device or personal computer. Further, in various embodiments, the type of display may be selected based on the nature of the task to be performed.

For a task that is performed across a range of different locations within a space, such as separate woodworking, metalworking, and electronics spaces, multiple displays may be deployed to provide area-relevant information for each of the different locations. Alternatively, the various spaces may be equipped with a docking station, whereby a mobile device presents information relevant to a particular work space when placed into the corresponding docking station. For tasks that are performed on site rather than at a centrally located workbench, one or more mobile devices may be deployed to provide onsite assistance at the work where the task is performed.

For a task that is performed at a single centrally located workspace, a single fixed, large display, such as a digital whiteboard, may be deployed. Such a fixed, large display may be physically positioned horizontally as a smart workbench or vertically mounted on a wall. Alternatively, the display may be projected to provide relevant information on any appropriate surface. Finally, head-mounted displays may be used to provide view-specific overlays or peripheral information.

In some embodiments, the workspace guidance engine 232 augments the displayed visual information with audio or tactile information. For example, the workspace guidance engine 232 could provide audio instructions or prompt the maker to review the visual information in a particular portion of the display. The workspace guidance engine 232 could receive tactile input, such as from a touch screen display, or provide tactile feedback to the maker in the form of a vibration, pulse, or other tactile response.

As further described herein, the workspace guidance engine 232 communicates with augmented tools, safety glasses, toolkits, and automated recording devices to monitor, record, and respond to physical actions of makers in real time. The workspace guidance engine 232 provides workflow monitoring and the delivery of interactive tutorials. The workspace guidance engine 232 thereby delivers a context-rich, multi-faceted instructional experience for a novice or intermediate-level maker. In addition, the workspace guidance engine 232 provides an informed and safe environment in existing machine shops and maker spaces where initial maker skills can be learned and refined.

The safety glass engine 234 receives status information as to when a pair of safety glasses, augmented with a network interface, is being worn by a maker. A specially equipped pair of safety glasses transmits a signal to the safety glass engine 234 indicating whether the maker is wearing or not wearing the safety glasses. The safety glasses may transmit a signal via a wired or wireless connection. The safety glass engine 234 notifies the workspace guidance engine 232 as to when the maker is wearing or not wearing the safety glasses. If the workspace guidance engine 232 determines that the current task step involves use of a dangerous piece of equipment or an otherwise dangerous condition, and the workspace guidance engine 232 receives a signal from the safety glass engine 234 that the maker is not wearing safety glasses, then the workspace guidance engine 232 performs an appropriate action, including, without limitation, notifying the maker of the need to wear safety glasses, disabling the dangerous equipment, or changing an operating condition of the dangerous equipment, such as reducing the speed or temperature of the dangerous equipment.

The augmented tool engine 236 receives status information from one or more augmented tools, where each tool is augmented with a network interface, and transmits control information to the augmented tools. The augmented tool engine 236 receives status information relevant to the particular tool, including, without limitation, the on/off status, operating temperature, operating speed, accessory status, and operating voltage or current of a particular augmented tool. As one non-limiting example of an accessory status, the augmented tool engine 236 could receive information regarding the size of a drill bit inserted or installed in an augmented drill or precision rotary tool. The augmented tool engine 236 transmits relevant status information received from the augmented tools to the workspace guidance engine 232. In response, the augmented tool engine 236 receives control information from the workspace guidance engine 232. The augmented tool engine 236 transmits the control information to the appropriate augmented tool, including, without limitation, a command to turn on or off, a command to operate at a particular speed, and a command to operate at a particular temperature. The augmented tool engine 236 transmits the control information to the appropriate augmented tool to operate an augmented tool to aid the maker in completing a particular step and to disable or change the operation of an augmented tool when the maker is operating the augmented tool in an unsafe manner.

The toolkit guidance engine 238 receives information from the workspace guidance engine 232 as to which tool or parts is needed to perform the current step in a task. The toolkit guidance engine 238 transmits information regarding the needed tool or part to a toolkit augmented with a network interface. The augmented toolkit provides an indication as to where the needed tool or part is located. For example, the augmented toolkit could illuminate an LED located on the bin in the augmented toolkit that contains the tool or part. The augmented toolkit is equipped with a sensor for each bin to determine when the needed tool or part is removed from the bin. In some embodiments, the augmented toolkit may be equipped with a single sensing system that simultaneously monitors each bin to determine when any tool or part is removed and to identify the particular bin or bins from which a tool or part was removed. For example, such a sensing system could include a depth sensing camera that would simultaneously detect removal of a tool or part from any one or more of the bins in the augmented toolkit.

The augmented toolkit can sense removal of a tool or part via any technically feasible approach, including, without limitation, via a depth sensor for sensing when a hand is placed in the bin, a weight sensor for determining the weight of a bin, and a radio frequency identification (RFID) embedded within a tool or part for determining the distance of the tool or part from the bin. In a similar manner, the augmented toolkit determines when a tool or part has been returned and placed back into the bin in the toolkit. The toolkit guidance engine 238 receives information regarding removal and replacement of a tool or part from the augmented toolkit and, in turn, transmits the removal and replacement information to the workspace guidance engine 232. In this manner, the toolkit guidance engine 238, along with the augmented toolkit, aids the maker in locating an appropriate tool or part for each step in a task.

Figure 3:
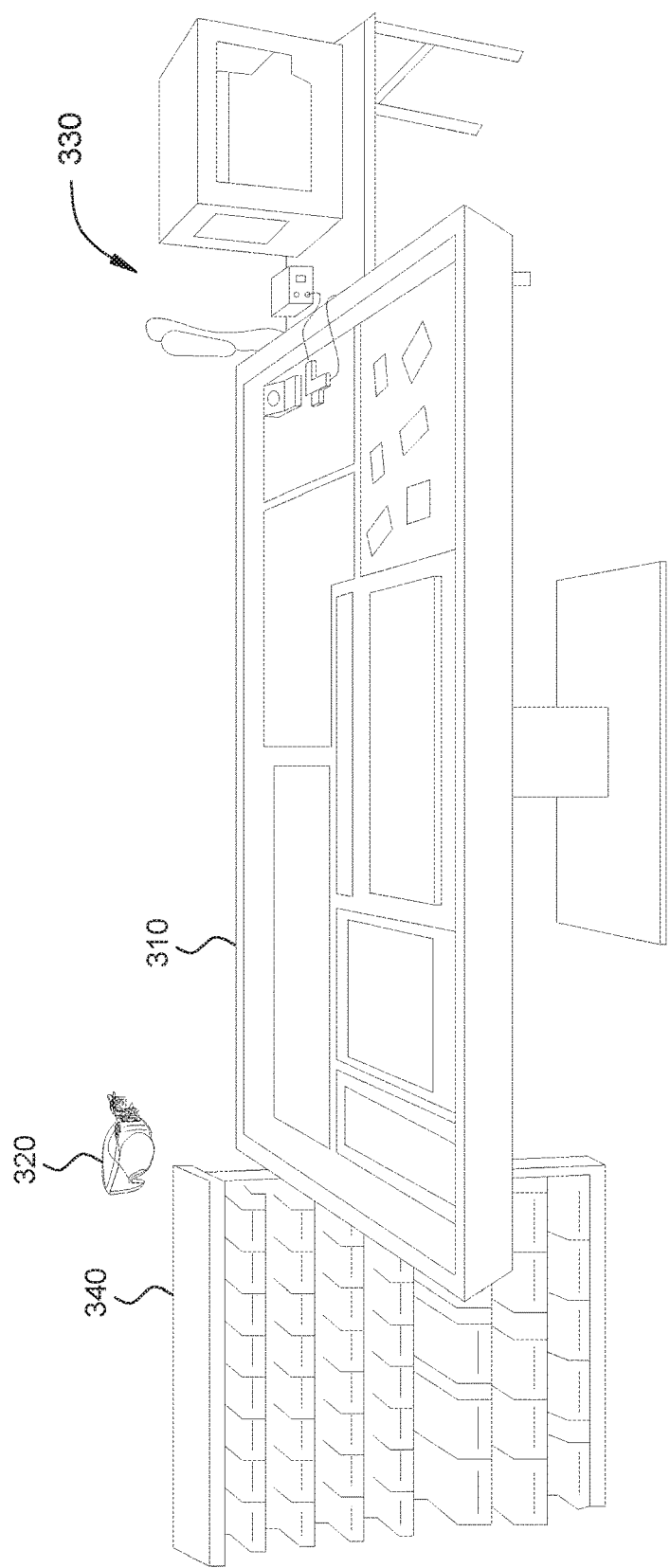
FIG. 3 illustrates a configuration of the smart workspace system of FIG. 2, according to various embodiments of the present invention.

FIG. 3 illustrates a configuration of the smart workspace system of FIG. 2, according to various embodiments of the present invention. As shown, the configuration includes, without limitation, an augmented workbench 310, augmented safety glasses 320, one or more augmented tools 330, and an augmented toolkit 340.

The augmented workbench 310 includes information panels that are presented to the maker, where the information panels are provided by the workspace guidance engine 232. The augmented workbench 310 provides the information panels via any technically feasible approach, including, without limitation, a horizontally or vertically mounted display, a projection system that projects an image onto a surface, a mobile device with an integrated display, or a head-mounted display. In some embodiments, the augmented workbench 310 may include a depth-sensing camera (not explicitly shown) to enable object tracking and touch interaction to further sense the operations performed by the maker and to aid in providing improved feedback and instructions to the maker. The augmented workbench 310 communicates with the workspace guidance engine 232 via a wired or wireless communications channel.

In some embodiments, the augmented workbench 310 may provide reinforcing and warning audio feedback based on various events. The augmented workbench 310 may provide a positive audio tone for correct tool usage, such as when the maker turns a 3D printer, and when a process is complete, such as when 3D printing task is complete. Likewise, the augmented workbench 310 may provide a positive audio tone for correct tool usage when a tool is ready for use, such as when a glue gun or soldering iron has reached an operating temperature. In addition, the augmented workbench 310 may provide a warning tone and corresponding visual cues should safety glasses be needed or if a tool is used incorrectly, such as when a drill is operated at an excessive speed. The volume of the audio alerts may be dynamically adapted to account for any tools that are currently being used. For example, the tone alerting that the drill is being used too fast may be relatively loud to account for the sound of the drill. Correspondingly, the tone reminding the maker to wear safety glasses when removing the soldering iron from the holster may be relatively quiet.

The augmented safety glasses 320 are equipped with a sensor to determine when the maker is wearing the augmented safety glasses 320 and when the maker is not currently wearing the augmented safety glasses 320. The augmented safety glasses 320 transmit this information to the safety glass engine 234. The safety glass engine 234, in turn, transmits the information to the workspace guidance engine 232 for further action. In response, the workspace guidance engine 232 performs an appropriate action, including, without limitation, providing a visual, audio, or tactile warning to the maker, causing an augmented tool 330 to be disabled, or causing an augmented tool 330 to change one or more operating conditions. The augmented safety glasses 320 communicate with the safety glass engine 234 via a wired or wireless communications channel.

The augmented tools 330 are equipped with one or more sensors to determine operating conditions of the augmented tools 330, including, without limitation, the on/off status, the operating temperature, accessory status, and the operating voltage or current of the augmented tools 330. As one non-limiting example of an accessory status, the augmented tool 330 could be equipped with a sensor that monitors and indicates the size of a drill bit inserted or installed in an augmented drill or precision rotary tool.

The augmented tools 330 transmit this information to the augmented tool engine 236. The augmented tool engine 236, in turn, transmits the information to the workspace guidance engine 232 for further action. In response, to the workspace guidance engine 232 performs an appropriate action, including, without limitation, providing a visual, audio, or tactile message to the maker regarding status of the augmented tool 330, causing an augmented tool 330 to be disabled, or causing an augmented tool 330 to change one or more operating conditions. The workspace guidance engine 232 causes an augmented tool to be disabled or to change operating conditions by transmitting a message to the augmented tool engine 236. The augmented tool engine 236, in turn, transmits the message to the augmented tool 330 to disable or change operation conditions of the augmented tool 330. The augmented tools 330 communicate with the augmented tool engine 236 via a wired or wireless communications channel.

The augmented toolkit 340 includes a set of bins, where each bin contains one or more tools or parts of a given type. Each bin in the augmented toolkit 340 includes an indicator, such as an LED, to identify the location of a needed tool or part. Each bin in the augmented toolkit 340 also includes a sensor to determine when a tool or part has been removed from the bin and returned and placed back into the bin. When a particular tool or part is needed to complete a particular step, the workspace guidance engine 232 transmits a message to toolkit guidance engine 238 to locate the needed tool or part. The toolkit guidance engine 238 transmits a corresponding message to the augmented toolkit 340. In response, the augmented toolkit 340 identifies the bin where the tool or part is located, for example, by lighting an indicator on the appropriate bin. The augmented toolkit 340 transmits a message to the toolkit guidance engine 238 when the tool or part has been removed from the bin and again when the tool or part is returned and placed back into the bin. The augmented toolkit 340 transmits a corresponding message to the workspace guidance engine 232.

In some embodiments, the augmented toolkit 340 may remove the identification of the bin when the tool or part is returned and placed back into the bin. In such embodiments, the indicator may remain illuminated after the tool or part is removed from the bin and until the tool or part is replaced into the bin. In some embodiments, the identification of the bin may be removed when the tool or part is removed from the bin. In such embodiments, the indicator may illuminate again when the maker has finished using the tool or part. The indicator may be removed when the tool or part is returned and placed back into the bin. Alternatively, the augmented toolkit 340 may remove the identification in response to a message received from the toolkit guidance engine 238. The augmented toolkit 340 communicates with the toolkit guidance engine 238 via a wired or wireless communications channel.

Figure 4:
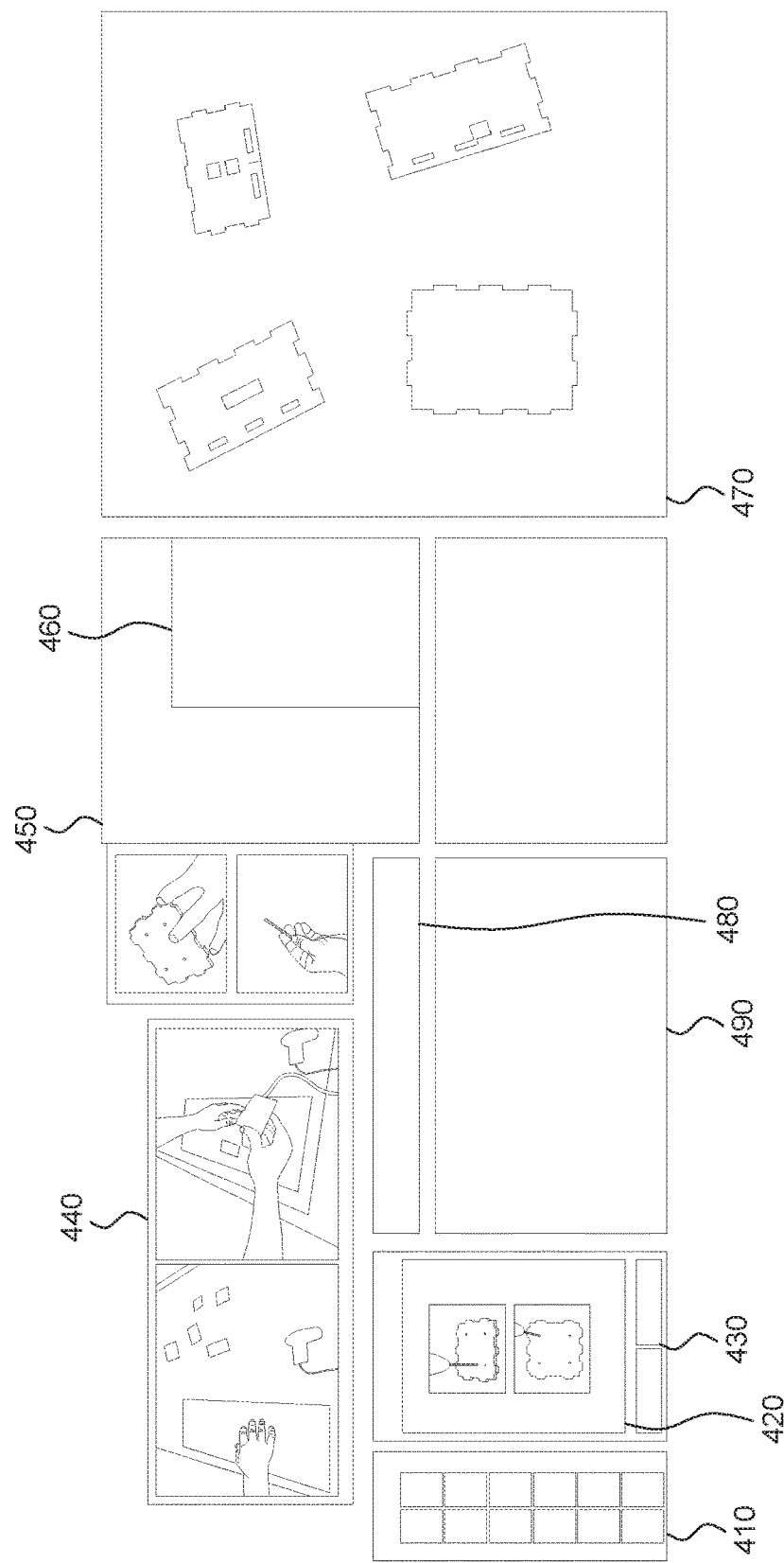
FIG. 4 illustrates various information panels that can be displayed by the smart workspace system of FIG. 2, according to various embodiments of the present invention.

FIG. 4 illustrates various information panels that are displayed by the smart workspace system of FIG. 2, according to various embodiments of the present invention. Although a particular set of information panels is shown in a particular arrangement, other information panels and arrangements are possible and within the scope of the present invention. As shown, the set of information panels includes, without limitation, an overview panel 410, a current step panel 420, a navigation panel 430, a video clip panel 440, a tool use panel 450, a tool status panel 460, a parts panel 470, a warning panel 480, and a work surface panel 490.

The overview panel 410 illustrates the set of steps, or a portion of the steps, for completing a task. The overview panel 410 provides a quick reference to the series of steps in a given task and may be used to access any portion of the instructions for the set of steps for the task. As shown, the overview panel 410 includes, without limitation, a thumbnail image corresponding to the step. Alternatively, the overview panel 410 illustrates the steps through any other technically feasible approach, including, without limitation, a textual list of steps or a graphical illustration of the steps. One of the steps in the overview panel may be highlighted to indicate the current step.

The current step panel 420 includes information regarding how to complete the current step in any technically feasible form, including, without limitation, textual information, static images, and graphical representations. The information in the current step panel 420 is scrollable by the maker to access various portions of the information pertaining to the current step.

The navigation panel 430 includes controls for the maker to advance to the next step or return to a previous step. By pressing the next and previous buttons in the navigation panel 430, the maker can change the information in one or more information panels to provide information appropriate to any of the steps shown in the overview panel 410.

The video clip panel 440 provides domain knowledge in the form of video clips to assist the maker in performing the current step. Typically, the video clip panel 440 displays videos of other users performing the current task. These videos clips provide additional cues supplemental to the information in the current step panel 420 in order to assist the maker with trouble-shooting and demonstrating the variation in approaches to completing the current step. The video clips provide novice makers with broader knowledge of a current task. The video clips may be presented with a side view, as is typical for instructional video clips. Alternatively, the video clips may be presented with an overhead view in order to provide first-person point of view of the current step.

The tool use panel 450 provides information on the safe use of any tools needed to complete the current step. The information may be in any technically feasible form, including, without limitation, textual information, video clips, still images, and graphical information. For example, if a soldering iron is needed for the current step, the tool use panel displays an explanation of how to properly use a soldering iron, including best practices, safety tips, and troubleshooting advice.

The tool status panel 460 identifies one or more tools needed to complete the current step. The tool status panel 460 prompts the maker to turn relevant tools on or off either before the tools are needed or once the tools have been used for a particular step. The tool status panel 460 also provides information on the current operation of various tools, including, without limitation, on/off status, operating temperature, accessory status, operating voltage or current, and whether a tool is ready for use or has completed a particular operation. In one example, the tool status panel 460 could indicate the status of a 3D printer as currently printing and the status of a soldering iron as hot and ready to use. In another example, the tool status panel 460 could indicate information regarding the size of a drill bit inserted or installed in an augmented drill or precision rotary tool.

The parts panel 470 shows images or graphical images of the parts needed to perform a particular task. At each step of the task, the parts panel 470 tracks, highlights, identifies, and annotates the parts needed for the current step. The warning panel 480 provides warning information to the maker regarding certain safety issues. For example, the warning panel 480 could instruct the maker to wear safety glasses when performing the current step. The work surface panel 490 provides an area where the maker can perform a step without obscuring information displayed in the other information panels. In some embodiments, the work surface panel 490 may be centrally located on the bottom edge of the set of information panels, thereby providing easy access to the maker and easy readability of the information in the other information panels.

Figure 5:
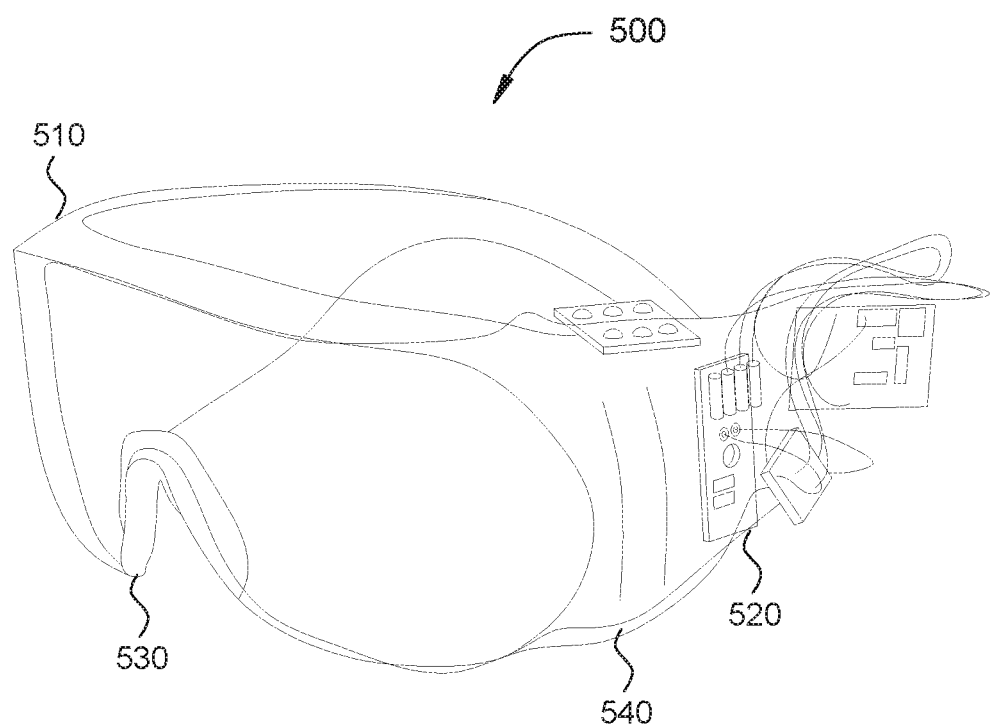
FIG. 5 illustrates a pair of augmented safety glasses configured to communicate with the smart workspace system of FIG. 2, according to various embodiments of the present invention.

FIG. 5 illustrates a pair of augmented safety glasses 500 configured to communicate with the smart workspace system of FIG. 2, according to various embodiments of the present invention. As shown, the augmented safety glasses 500 include, without limitation, safety glasses 510, a controller 520, and a conductive strip 530.

The safety glasses 510 protect the eyes of the maker when the maker is operating a dangerous piece of equipment or when performing a dangerous operation. In order to ensure that the maker is wearing the safety glasses 510 under such circumstances, a controller 520 is fitted to the glasses.

The controller 520 includes a processor that is connected to a memory, an input/output (I/O) interface, and a network interface (not explicitly shown). The processor may be any technically feasible form of processing device configured to process data and execute program code. The processor could be, for example, a central processing unit (CPU), a graphics processing unit (GPU), an application-specific integrated circuit (ASIC), a field-programmable gate array (FPGA), and so forth. In operation, the processor in the controller 520 executes an application program stored in the memory to perform one or more operations, as described herein. Upon executing the application program, the processor communicates with one or more external devices via the I/O interface. Upon executing the application program, the processor also exchanges messages with a remote machine via the network interface. The augmented safety glasses 500 may communicate with a remote machine via a wired or wireless connection. In some embodiments, the remote machine may be the smart workspace system 200 as described herein in conjunction with FIG. 2. In some embodiments, the remote machine may be an augmented tool as described herein in conjunction with FIG. 6.

For example, the processor could receive a signal from a sensor via the I/O interface, where the sensor could indicate a particular status or operating condition, including, without limitation, contact with the skin of the maker. In response, the processor could exchange messages with a remote machine via the network interface, where at least some of the messages could be associated with the signal received from the sensor.

More particularly, the controller 520 receives a signal from the conductive strip 530 when the conductive strip 530 is in contact with a conductive surface, such as skin. That is, when the maker wears the safety glasses 510, the conductive strip 530 makes contact with the nose of the maker and transmits a signal to the controller 520 via connector wire 540 and via the I/O interface within the controller 520. When the maker is not wearing the safety glasses 510, the conductive strip 530 does not make contact with the nose of the maker and, therefore, does not transmit a signal to the controller 520. In response, the controller 520 transmits, via the network interface within the controller 520, a message indicating whether the maker is currently wearing the safety glasses 510 or not. As an alternative to the conductive strip 530, the augmented safety glasses 500 may employ any other technically feasible approach, such as a small camera pointing inward to detect one or both of the eyes of the maker when wearing the augmented safety glasses 500.

Safety is a major concern for machine and power tools operation either in a public or private makerspace. Safety glasses provide important safety for the eyes of the maker when operating certain equipment or performing certain operations. However, makers sometimes forget to wear safety glasses, place safety glasses above the forehead and forget to put the safety glasses back over their eyes, or not realize that safety glasses should be worn when operating a specific tool or machine. Even if a maker is alerted to wear the safety glasses, the maker may ignore such warnings, resulting in increased risk of injury and potential liability. The augmented safety glasses 500 automatically recognize when a maker is not wearing the augmented safety glasses 500, so that appropriate warnings can be provided and tools and equipment can be disabled or operated safely.

The augmented safety glasses 500 communicate either to the safety glass engine 234 in the smart workspace system 200 or directly to one or more augmented tools 330. If the maker is not wearing the augmented safety glasses 500, the maker may, upon turning on a potentially dangerous piece of equipment, receive a visual, audio, or tactile warning that safety glasses should be worn when operating the equipment. In addition or in the alternative, the equipment may be disabled or may operate at a reduced speed or temperature if the maker is not wearing the augmented safety glasses 500.

The sensors and controller for the augmented safety glasses 500 may be built into the augmented safety glasses 500 during manufacturing and assembly. Alternatively, a pair of safety glasses may be refitted in the field with one or more sensors and a controller, thereby converting a conventional pair of safety glasses into augmented safety glasses 500.

Figure 6:
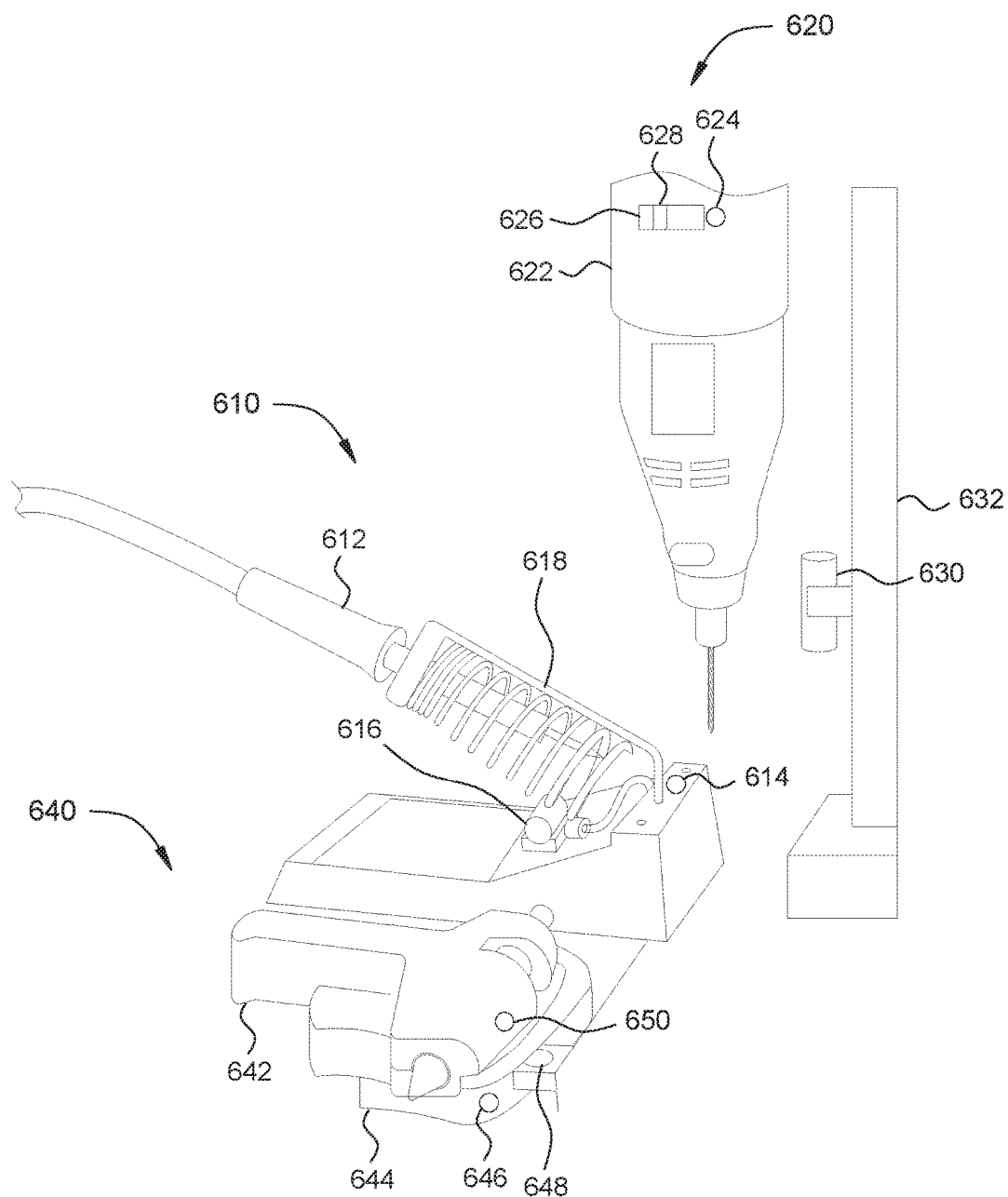
FIG. 6 illustrates augmented tools configured to communicate with the smart workspace system of FIG. 2, according to various embodiments of the present invention.

FIG. 6 illustrates augmented tools configured to communicate with the smart workspace system of FIG. 2, according to various embodiments of the present invention. As shown, the augmented tools include, without limitation, an augmented soldering iron 610, an augmented precision rotary tool 620, and an augmented glue gun 630.

As described herein, augmented tools include a controller that, in turn, includes a processor that is connected to a memory, an input/output (I/O) interface, and a network interface (not explicitly shown). The processor may be any technically feasible form of processing device configured to process data and execute program code. The processor could be, for example, a central processing unit (CPU), a graphics processing unit (GPU), an application-specific integrated circuit (ASIC), a field-programmable gate array (FPGA), and so forth. In operation, the processor in the controller executes an application program stored in the memory to perform one or more operations, as described herein. Upon executing the application program, the processor communicates with one or more external devices via the I/O interface. Upon executing the application program, the processor also exchanges messages with a remote machine via the network interface. Augmented tools may communicate with a remote machine via a wired or wireless connection. In some embodiments, the remote machine may be the smart workspace system 200 as described herein in conjunction with FIG. 2.

For example, the processor could receive a signal from a sensor via the I/O interface, where the sensor could indicate a particular status or operating condition, including, without limitation, the on/off and heating status of a tool or other device, the current speed or temperature of the tool or device, and whether the tool or device is placed in a corresponding holster. In response, the processor could exchange messages with a remote machine via the network interface, where at least some of the messages could be associated with the signal received from the sensor. Further, the processor could exchange messages with a remote machine via the network interface, where at least some of the messages could be associated with the signal received from the sensor. Likewise, the processor could exchange messages with a remote machine via the network interface, where at least some of the messages could be associated with disabling or otherwise changing an operating condition of a tool or device. In response, the processor could transmit a signal to an actuator via the I/O interface, where the actuator could disable or otherwise change an operating condition of the tool or device, including, without limitation, removing power from the tool or device, changing the operating speed of the tool or device, or changing the operating temperature of the tool or device.

More particularly, augmented tools include sensors and actuators that support capture, location, control, and actuation operations. For example, information could be captured from an augmented tool via status sensors to determine when and how an augmented tool is being used. Location based sensors could enable augmented tools to be located, where the smart workspace system 200 guides the maker towards a particular augmented tool if the maker is unsure as to what the augmented tool looks like or where the augmented tool is located. The smart workspace system 200 could control the use of an augmented tool by causing the augmented tool to be disabled or to change an operating condition such as a speed or a temperature. Finally, the smart workspace system 200 could control actuators on the augmented tool in order to assist the maker by configuring or operating the augmented tool on behalf of or in cooperation with the maker, based on the context of a current task. For example, if the maker is recreating an object previously built by another maker, the smart workspace system 200 could set the operating speed of a drill, based on the settings used by the other maker when building the object.

The sensors, actuators, and controller for a particular augmented tool may be built into the augmented tool during manufacturing and assembly. Alternatively, a tool may be refitted in the field with one or more sensors, actuators, and controller, thereby converting a conventional tool into an augmented tool.

The augmented soldering iron 610 includes, without limitation, a soldering iron 612, a precision light sensor 614 placed over the power light (not explicitly shown) of the soldering iron 612, and a controller (not explicitly shown). The precision light sensor 614 detects when the power light is dark, indicating that the soldering iron 612 is off; constantly illuminated, indicating that the soldering iron 612 is heating; or flickering, indicating that the soldering iron 612 has reached the operating temperature. The augmented soldering iron 610 also includes a proximity sensor 616 placed beneath the holster 618 of the soldering iron 612 that detects whether the soldering iron 612 is present in the holster 618 or has been removed from the holster 618.

The controller receives signals from each of the precision light sensor 614 and the proximity sensor 616 regarding the operating conditions of the augmented soldering iron 610. When the controller detects a change in the precision light sensor 614 or the proximity sensor 616, the controller transmits a message to a remote machine. In some embodiments, the controller receives a message from the remote machine to disable or change an operating condition of the augmented soldering iron 610. In response, the controller transmits a signal to one or more actuators (not explicitly shown) to disable the augmented soldering iron 610 or to change an operating condition of the augmented soldering iron 610, such as changing the operating temperature.

The augmented precision rotary tool 620 includes a precision rotary tool 622, a hall-effect sensor 624, a magnet 626 attached to the variable speed power switch 628, and a controller (not explicitly shown). The augmented precision rotary tool 620 detects the operating speed of the precision rotary tool 622 by measuring the effect of the magnet 626 on the hall-effect sensor 624 based on the position of the variable speed power switch 628. The augmented precision rotary tool 620 also includes a proximity sensor 630 integrated into the stand 632. The proximity sensor 630 detects when the precision rotary tool 622 is present in the stand 632. Likewise, the proximity sensor 630 detects when the precision rotary tool 622 has been removed from the stand 632, such as when the maker uses the precision rotary tool 622 to perform certain handheld operations.

The controller receives signals from each of the hall-effect sensor 624 and the proximity sensor 630 regarding the operating conditions of the augmented precision rotary tool 620. When the controller detects a change in the hall-effect sensor 624 or the proximity sensor 630, the controller transmits a message to a remote machine. In some embodiments, the controller receives a message from the remote machine to disable or change an operating condition of the augmented precision rotary tool 620. In response, the controller transmits a signal to one or more actuators (not explicitly shown) to disable the augmented precision rotary tool 620 or to change an operating condition of the augmented precision rotary tool 620, such as changing the operating speed.

The augmented glue gun 640 includes a glue gun 642, a holster 644, and a controller (not explicitly shown). The holster 644 includes a temperature sensor 646 that detects the current temperature of the glue gun 642 when the glue gun 642 is placed in the holster 644. The holster 644 also includes a hall-effect sensor 648 that detects the effect of a magnet 650 mounted on the glue gun 640 in order to determine whether the glue gun 642 is present in the holster 644 or has been removed from the holster 644.

The controller receives signals from each of the temperature sensor 646 and the hall-effect sensor 648 regarding the operating conditions of the augmented glue gun 640. When the controller detects a change in the temperature sensor 646 and the hall-effect sensor 648, the controller transmits a message to a remote machine. In some embodiments, the controller receives a message from the remote machine to disable or change an operating condition of the augmented glue gun 640. In response, the controller transmits a signal to one or more actuators (not explicitly shown) to disable the augmented glue gun 640 or to change an operating condition of the augmented glue gun 640, such as changing the operating temperature.

In addition to the augmented tools illustrated in FIG. 6, other types of augmented tools may be instrumented with varying types of sensors, actuators, and controller within the scope of the present invention. As one example, and without limitation, an augmented 3D printer (not explicitly shown) could be fitted a voltage or current monitor attached to the power cable of the augmented 3D printer. The operating voltage or current could identify the operating state of the augmented 3D printer, where: (1) a low, constant voltage could indicate that the augmented 3D printer is on and ready; (2) a medium, fluctuating voltage could indicate that the augmented 3D printer is heating; (3) a high, fluctuating voltage could indicate that the augmented 3D printer is currently printing; and (4) a low, constant voltage could indicate that the augmented 3D printer has completed a print operation and is ready for another print operation.

Makerspaces often include a variety of physical tools and equipment. Often, the use of such tools and equipment is challenging for novice and intermediate makers. As a result, makers may not realize whether they are using a tool or piece of equipment properly within the context of their current task. For example, a maker could use the wrong drill or drill bit for a particular step, or may use the drill at the wrong speed setting. A maker could attempt to operate a soldering iron or a glue gun before the soldering iron or glue has properly preheated to the correct operating temperature. Further, tools often do not provide adequate safety alerts when the tool is being operated in an unsafe manner. For example, a maker could be operating a drill at a speed that is too high for the type of drill bit or the particular material being drilled. A maker could forget to turn off a soldering iron or a glue gun when the soldering iron or glue gun is no longer needed. Although some tools have LEDs or other indicators to help inform the maker of the tool status, these indicators are often uninformative or go unnoticed by the maker.

Augmented tools provide operational information to the smart workspace system 200 via a wired or wireless connection. The smart workspace system 200 thereby tracks usage metrics of tools and equipment and whether the tools and equipment are being used in a safe manner. The smart workspace system 200 provides helpful information and warnings to the maker and causes tools to be disabled or to change operating conditions. The smart workspace system 200 gathers usage data for reference by the makerspace manager to understand how the tools in the makerspace are being used, who can be alerted if any tools are being operated improperly. Because, the smart workspace system 200 is aware of the steps of the task being performed by the maker, the smart workspace system 200 can compare the sensor values of an augmented tool to the expected sensor readings for the current step. The smart workspace system 200 provides positive feedback to the maker when the correct sensor values are read, such as when the maker places the correct drill bit in a drill. The smart workspace system 200 provides negative feedback to the maker if improper readings are measured, such as when the maker operates the drill speed at an excessively high speed.

Figure 7:
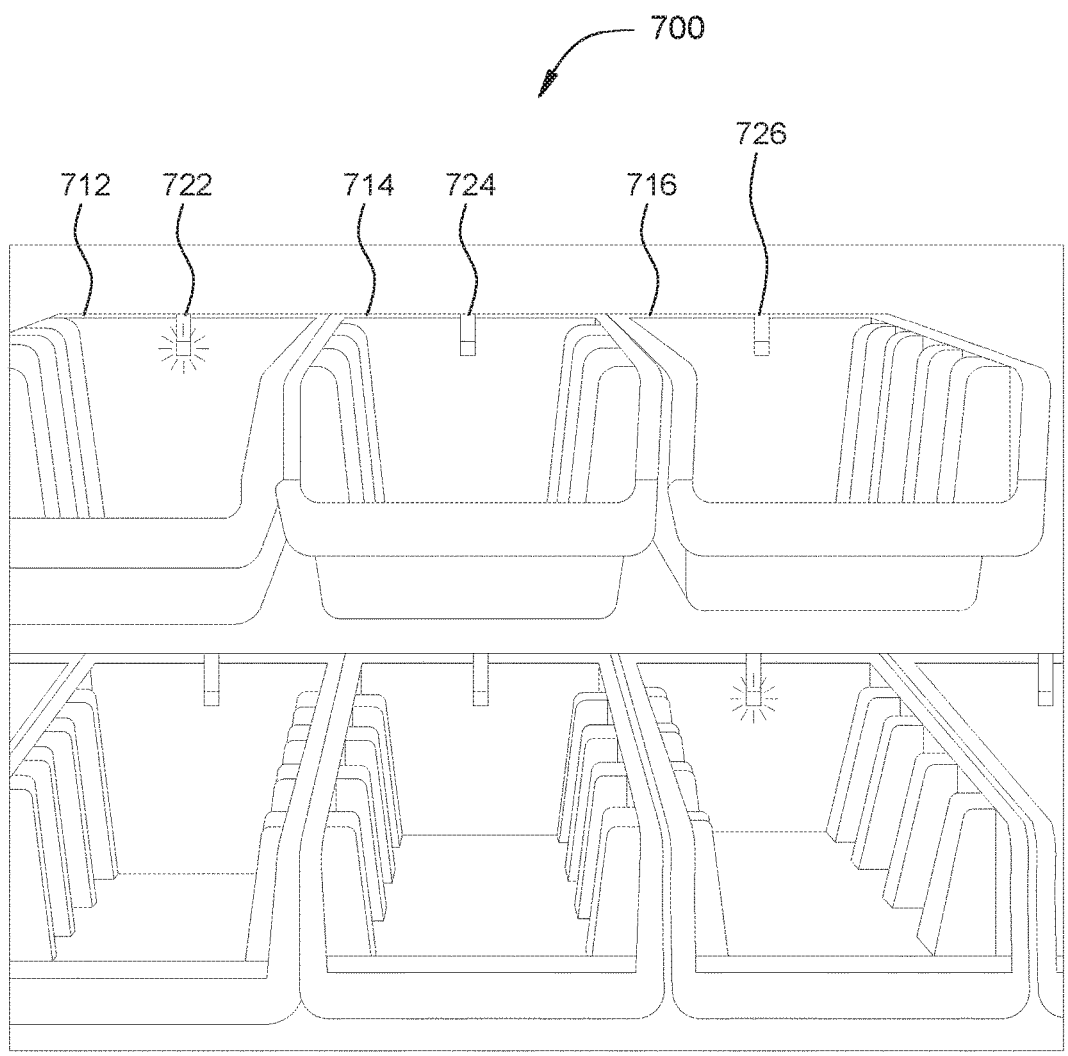
FIG. 7 illustrates an augmented toolkit configured to communicate with the smart workspace system of FIG. 2, according to various embodiments of the present invention.

FIG. 7 illustrates an augmented toolkit 700 configured to communicate with the smart workspace system of FIG. 2, according to various embodiments of the present invention. As shown, the augmented toolkit 700 includes, without limitation, multiple bins, such as bins 712, 714, and 716, each bin having a corresponding indicator 722, 724, and 726, and a corresponding sensor (not explicitly shown).

As described herein, an augmented toolkit includes a controller that, in turn, includes a processor that is connected to a memory, an input/output (I/O) interface, and a network interface (not explicitly shown). The processor may be any technically feasible form of processing device configured to process data and execute program code. The processor could be, for example, a central processing unit (CPU), a graphics processing unit (GPU), an application-specific integrated circuit (ASIC), a field-programmable gate array (FPGA), and so forth. In operation, the processor in the controller executes an application program stored in the memory to perform one or more operations, as described herein. Upon executing the application program, the processor communicates with one or more external devices via the I/O interface. Upon executing the application program, the processor also exchanges messages with a remote machine via the network interface. The augmented toolkit 700 may communicate with a remote machine via a wired or wireless connection.

In some embodiments, the remote machine may be the smart workspace system 200 as described herein in conjunction with FIG. 2.

For example, the processor could exchange messages with a remote machine via the network interface, where at least some of the messages could be associated with identifying a bin included in the toolkit, where the bin contains one or more of a particular tool or part. The processor, in turn, could transmit a signal via the I/O interface to illuminate an indicator, such as a light emitting diode, or activate, via an actuator, one or more other visual, audio, or tactile indicators, where such an indicator identifies a bin in the toolkit where a particular tool or part is located. The processor could then receive a signal from a sensor via the I/O interface, where the sensor could indicate that a tool or part has been removed from the bin. The sensor could be any technically feasible sensor, including, without limitation, a depth sensor for sensing when a hand is placed in the bin, a weight sensor for determining the weight of a bin, and a radio frequency identification (RFID) tag embedded within a tool or part for determining the distance of the tool or part from the bin.

The processor could likewise receive a signal from such a sensor via the I/O interface, where the sensor could indicate that a tool or part has been returned and placed back into the bin. The processor could transmit a signal via the I/O interface to extinguish or otherwise remove the indicator. The processor could remove the indicator upon the occurrence any technically feasible condition, including, without limitation, receiving a signal indicating that the tool or part has been removed from the bin, receiving a signal indicating that the tool or part has been returned and placed back into the bin, or receiving a message from a remote machine that includes a command to remove the indicator.

More particularly, each bin 712, 714, and 716 is configured to contain one or more tools or parts of a particular type. Typically, makerspaces and other workspaces contain a wide variety of tools or parts that makes need for various steps and tasks. In some cases, the maker needs a particular tool or part temporarily and returns the tool or part upon completion of the associated steps. In other cases, the maker needs a tool or part that is integrated into the final product or is consumed during the task and is, therefore, not returned. Often these tools and parts are organized into bins or shelves. Even with proper organization and labeling, the maker may have difficulty in finding a desired tool or part, particularly if the maker is a novice or is working in an unfamiliar makerspace. Further, when a maker retrieves an item, the maker may be unsure whether the retrieved item is the correct item or whether the maker retrieved the proper quantity of the item.

When the smart workspace system 200 determines that a particular tool or part is needed from the augmented toolkit 700, the smart workspace system 200 transmits a message to the augmented toolkit 700 to indicate the specific tool or part and the quantity needed. Alternatively, a maker requests a particular tool or part by entering the name and quantity of the tool or part into a user interface of either the smart workspace system 200 or the augmented toolkit 700. The augmented toolkit 700 receives the message or manual user input and, in response, lights the corresponding indicator 722, 724, and 726 according to the needed part. As shown, indicator 722 is illuminated, indicating that the bin 712 contains the needed tool or part. Indicators 724 and 726 are not illuminated, indicating that bins 714 and 726 do not contain the needed tool or part. When the maker retrieves the correct quantity and type of part, the augmented toolkit 700 may remove the indication by extinguishing indicator 722. Alternatively, the augmented toolkit 700 may continue to illuminate the indicator 722 until the maker returns the tool or part and places to the tool or part back into the bin 712.

By clearly indicating the correct tool and part locations, the augmented toolkit 700 reduces the uncertainty of novice and intermediate-level makers regarding correct tools or parts for specific steps of a task. Further, each bin is instrumented with a sensor to track when a maker retrieves a tool or part. For example, the sensor could be a depth sensor that detects when the hand of a maker enters a bin. The augmented toolkit 700 thereby knows when a maker has successfully obtained an item from a bin. Alternatively, the sensor could be a weight sensor at the bottom of each bin that detects the weight of the bin. Given a weight sensor with sufficient precision, the augmented toolkit could detect the quantity of items removed from each bin. Alternatively, the sensor could be an RFID sensor, where the corresponding tools or parts have an integrated RFID tag. The sensor would then detect when the corresponding tool or part is within the bin or within a threshold distance away from the bin. In cases where the quantity of an item is detectible, the augmented toolkit 700 could inform a makerspace manager when a bin is getting low on material and the corresponding tool or part should be reordered.

The sensors, indicators, actuators, and controller for the augmented toolkit 700 may be built into the augmented toolkit 700 during manufacturing and assembly. Alternatively, a toolkit may be refitted in the field with sensors, indicators, actuators, and a controller, thereby converting a conventional toolkit into an augmented toolkit 700.

It will be appreciated that the system shown herein is illustrative and that variations and modifications are possible. For example, although the augmented safety glasses, augmented tools, and augmented toolkit are described as communicating via a central smart workspace system, the augmented safety glasses, augmented tools, and augmented toolkit could communicate to each other via a peer-to-peer approach. That is, augmented safety glasses could communicate directly to an augmented tool regarding the status of the safety glasses. In response, the augmented tool could turn off or operate at a reduced speed if the maker is not currently wearing the safety glasses.

Figure 8A:
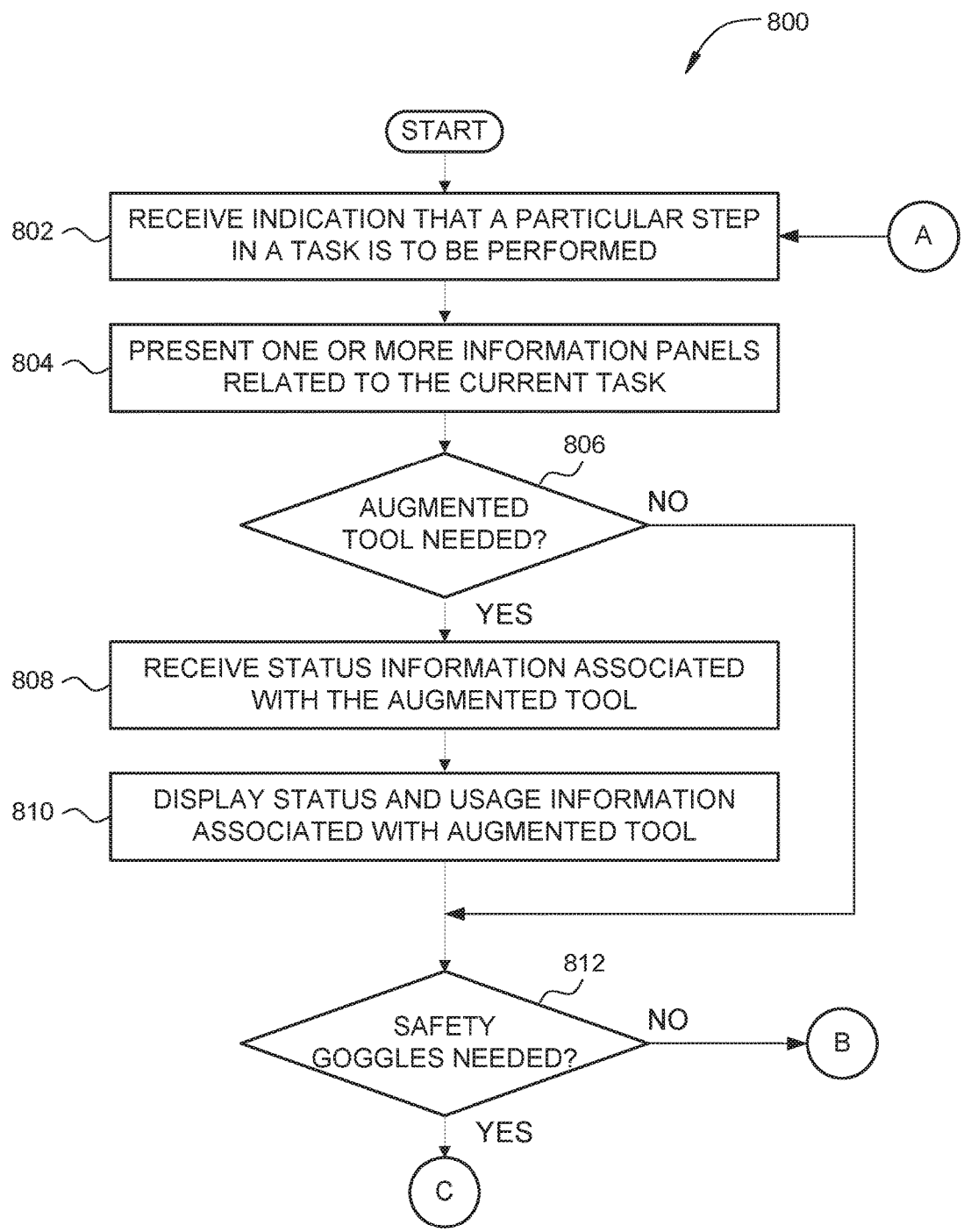
FIGS. 8A-8B set forth a flow diagram of method steps for assisting with performing a task within a smart workspace environment, according to various embodiments of the present invention.
Figure 8B:
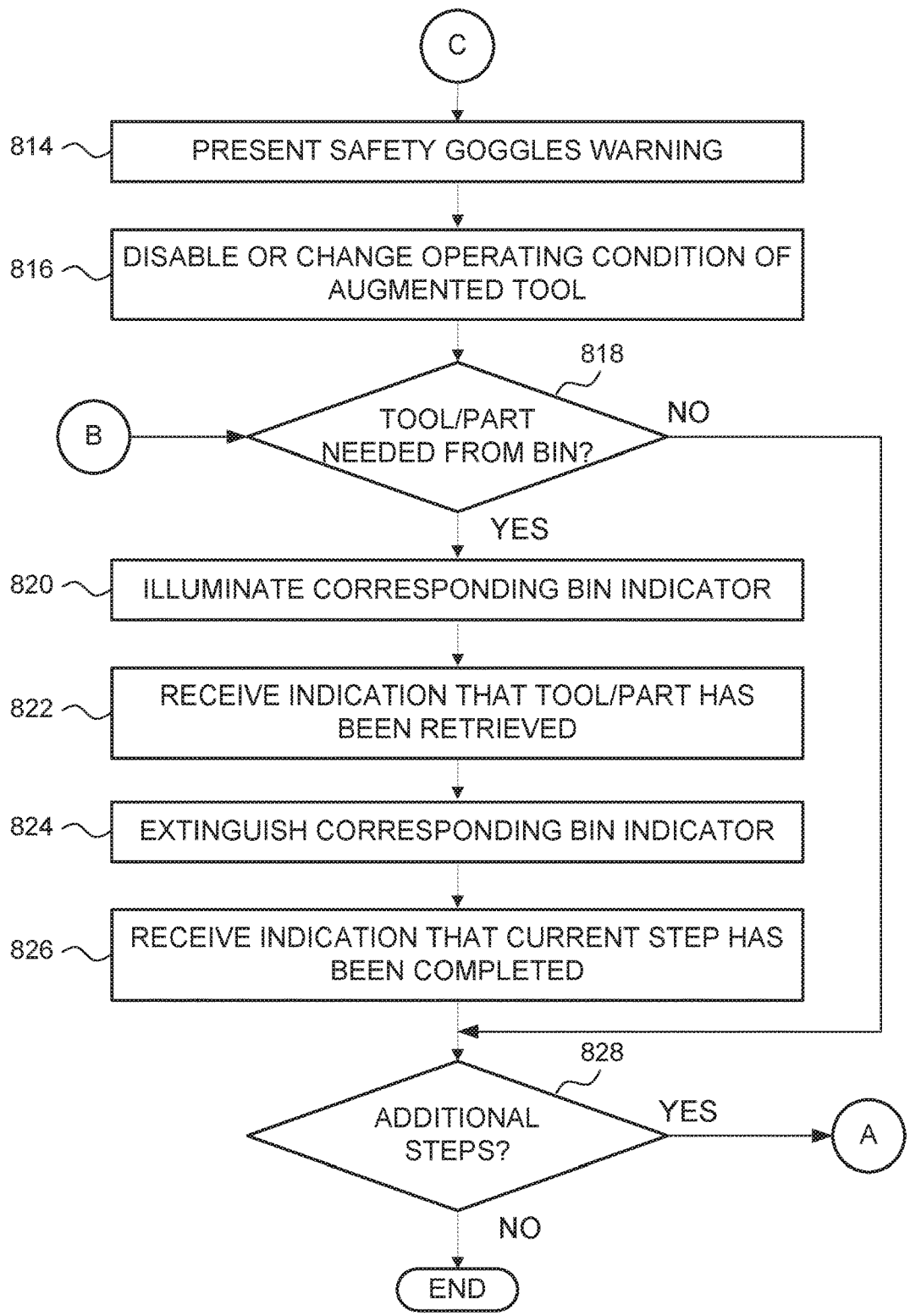

FIGS. 8A-8B set forth a flow diagram of method steps for assisting with performing a task within a smart workspace environment, according to various embodiments of the present invention. Although the method steps are described in conjunction with the systems of FIGS. 1-7, persons of ordinary skill in the art will understand that any system configured to perform the method steps, in any order, is within the scope of the present invention.

As shown, a method 800 begins at step 802, where the workspace guidance engine 232 determines that a particular step of a task is to be performed, referred to herein as the current step. At step 804, the workspace guidance engine 232 presents one or more information panels relevant to the current step. The information panels include, without limitation, an overview of the steps of the task, detailed instructions for the current task, video clips showing how the current task is performed, and an indication of the parts needed for the current task. At step 806, the workspace guidance engine 232 determines whether an augmented tool is needed to complete the current step. If an augmented tool is needed to complete the current step, then the method 800 proceeds to step 808, where the augmented tool engine 236 receives status information associated with the augmented tool. The augmented tool engine 236 transmits the status information to the workspace guidance engine 232. At step 810, the workspace guidance engine 232 displays the status information associated with the augmented tool along with information regarding how to properly and safely use the augmented tool.

At step 812, the workspace guidance engine 232 determines whether safety glasses are needed for the current step, but the maker is not currently wearing augmented safety glasses. In particular, the safety glass engine 234 receives status information from the augmented safety glasses as to whether or not the maker is currently wearing the augmented safety glasses. The safety glass engine 234 transmits this status information to the workspace guidance engine 232. If safety glasses are needed for the current step and the maker is not currently wearing the augmented safety glasses, then the method 800 proceeds to step 814, where the workspace guidance engine 232 provides a warning to the maker that safety glasses should be worn when performing the current step. The workspace guidance engine 232 may provide any combination of a visual, audio, or tactile warning to the maker. At step 816, the workspace guidance engine 232 directs the augmented tool engine 236 to disable the augmented tool or to change an operating condition of the augmented tool. The augmented tool engine 236, in turn, transmits a message to the augmented tool to disable the tool or to change an operating condition of the augmented tool, such as operating speed or operating temperature of the augmented tool.

At step 818, the workspace guidance engine 232 determines whether a tool or part stored within a bin of the augmented toolkit is needed to perform the current step. If a tool or part stored in a bin is needed to perform the current step, then the method 800 proceeds to step 820, where the workspace guidance engine 232 causes the toolkit guidance engine 238 to indicate the bin where the tool or part is stored. The workspace guidance engine 232 causes the toolkit guidance engine 238 to indicate the bin by transmitting a message to the toolkit guidance engine 238 with the specific tool or part needed along with the quantity needed. The toolkit guidance engine 238, in turn, transmits a message to the augmented toolkit indicating the identity and quantity of the needed tool or part. The augmented toolkit indicates the corresponding bin by illuminating an LED or by actuating some other indicator on the bin that stores the needed tool or part.

At step 822, the toolkit guidance engine 238 receives an indication from the augmented toolkit that the needed tool or part has been removed. The augmented toolkit detects removal of the tool or part via a sensor, such as a depth sensor, a weight sensor, or an RFID sensor. At step 824, the toolkit guidance engine 238 transmits a message to the augmented toolkit to cause the augmented toolkit to extinguish the LED or otherwise remove the indicator. The toolkit guidance engine 238 transmits a message to the workspace guidance engine 232 that the tool or part has been retrieved from the bin. At step 826, the workspace guidance engine 232 determines whether additional steps are needed to complete the current task. If additional steps are needed, then the method proceeds to step 802, described above. If no additional steps are needed, then the method 800 terminates.

Returning to step 818, if no tool or part stored in a bin is needed to perform the current step, then the method 800 proceeds to step 826, described above.

Returning to step 812, if safety glasses are not needed for the current step or if the maker is currently wearing the augmented safety glasses, then the method 800 proceeds to step 818, described above.

Returning to step 806, if no augmented tool is needed to complete the current step, then the method 800 proceeds to step 812 described above.

Figure 9:
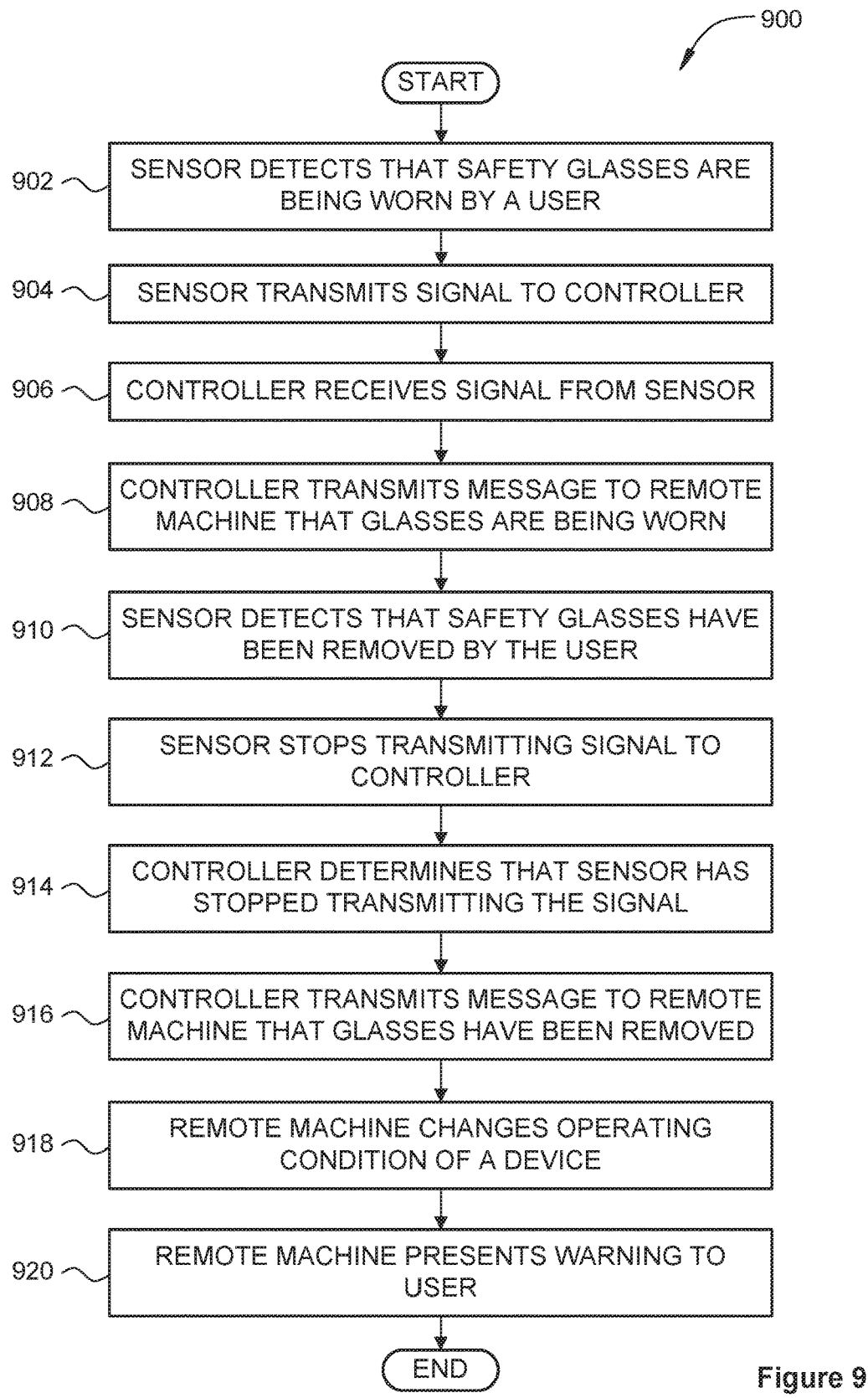
FIG. 9 is flow diagram of method steps for detecting whether the pair of augmented safety glasses of FIG. 5 are being worn by a user, according to various embodiments of the present invention.

FIG. 9 is flow diagram of method steps for detecting whether the pair of augmented safety glasses of FIG. 5 is being worn by a user, according to various embodiments of the present invention. Although the method steps are described in conjunction with the systems of FIGS. 1-7, persons of ordinary skill in the art will understand that any system configured to perform the method steps, in any order, is within the scope of the present invention.

As shown, a method 900 begins at step 902, where a sensor included in the augmented safety glasses detects that the safety glasses are being worn by a user. In one example, the augmented safety glasses could include a conductive strip that detects when the conductive sensor is in contact with skin, such as the nose of a user. In another example, the augmented safety glasses could include a camera that detects one or both eyes of the user when the augmented safety glasses are being worn by the user. At step 904, the sensor transmits a signal to a controller included in the augmented safety glasses. At step 906, the controller receives the signal from the sensor. At step 908, the controller transmits a first message to a remote machine indicating that the safety glasses are being worn by the user. In some embodiments, the remote machine may be the smart workspace system 200 as described herein in conjunction with FIG. 2. In some embodiments, the remote machine may be an augmented tool as described herein in conjunction with FIG. 6.

At step 910, the sensor detects that the safety glasses have been removed by the user. For example the sensor could detect that the conductive strip is no longer in contact with skin or that the camera no longer detects an eye of the user. At step 912, the sensor stops transmitting the signal to the controller. At step 914, the controller determines that the sensor has stopped transmitting the signal. At step 916, the controller transmits a second message to the remote machine indicating that the safety glasses have been removed by the user. At step 918, the remote machine changes an operating condition of a device. In one example, the remote machine disables the device from operating. In another example, the remote machine changes the operating speed of the device. In yet another example, the remote machine changes the operating temperature of the device. At step 920, the remote machine presents a warning to the user that the safety goggles should be worn. The warning may be in any technically feasible form, including, without limitation, a visual display, and audio signal, or a tactile signal. The method 900 then terminates.

Figure 10:
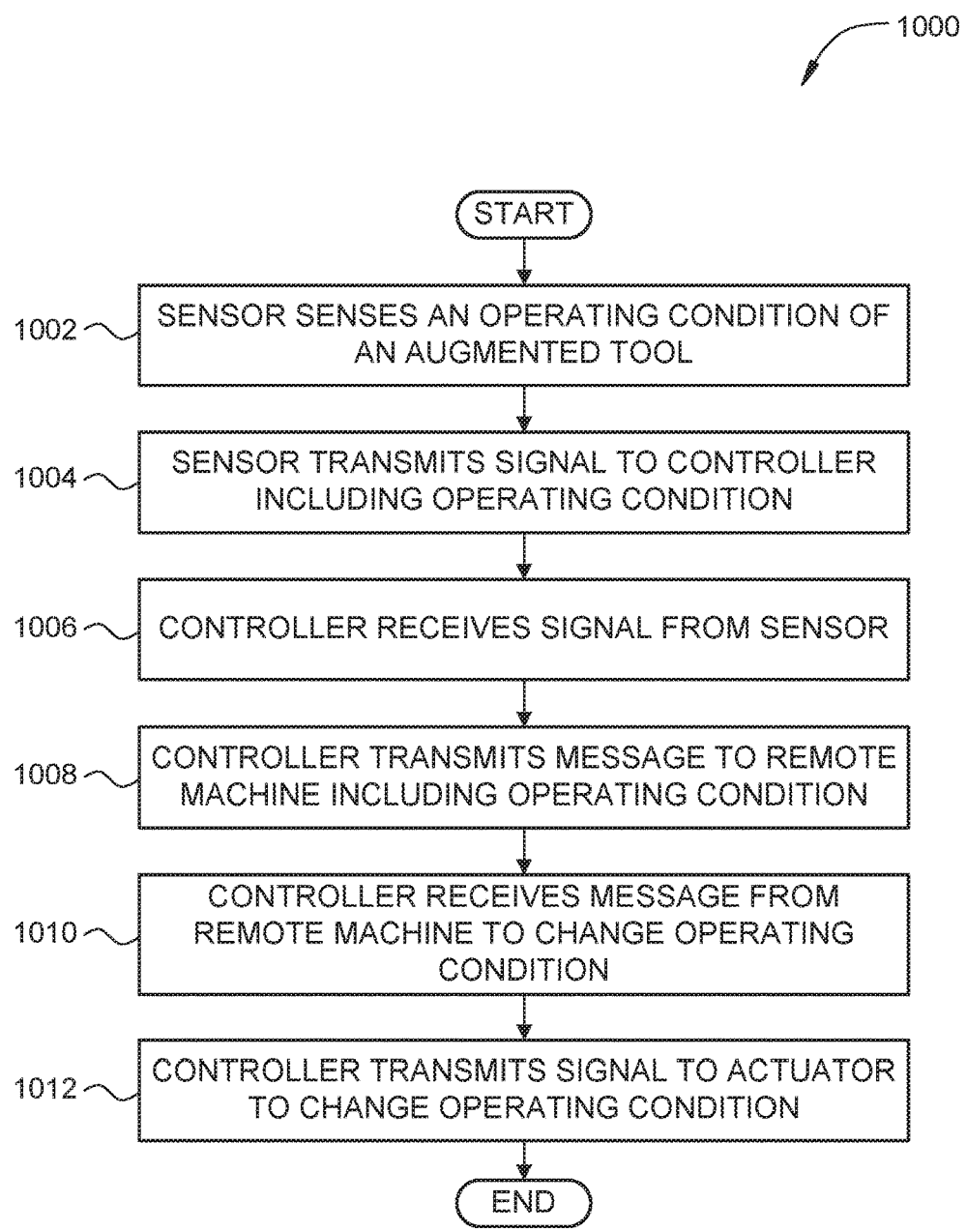
FIG. 10 is flow diagram of method steps for monitoring and controlling an augmented tool of FIG. 6, according to various embodiments of the present invention.

FIG. 10 is flow diagram of method steps for monitoring and controlling an augmented tool of FIG. 6, according to various embodiments of the present invention. Although the method steps are described in conjunction with the systems of FIGS. 1-7, persons of ordinary skill in the art will understand that any system configured to perform the method steps, in any order, is within the scope of the present invention.

As shown, a method 1000 begins at step 1002, where a sensor included in an augmented tool senses a first operating condition of a device associated with the augmented tool. In one example, the augmented tool could be an augmented soldering iron, and the sensor could sense whether the soldering iron is turned on or off, whether the soldering iron is currently heating to an operating temperature, or whether the soldering iron has been removed from a holster. In another example, the augmented tool could be an augmented precision rotary tool, and the sensor could sense the operating speed of the precision rotary tool or whether the precision rotary tool is present in a stand or has been removed from the stand. In yet another example, the augmented tool could be an augmented glue gun, and the sensor could sense the operating temperature of the precision rotary tool or whether the precision rotary tool is present in a holster or has been removed from the holster. In yet another example, the augmented tool could be an augmented 3D printer and the sensor could sense whether the 3D printer is idle, whether the 3D printer is currently heating to an operating temperature, whether the 3D printer is currently printing a 3D printing task, or whether the 3D printer has completed the 3D printing task.

At step 1004, the sensor transmits a signal to a controller included in the augmented tool that indicates the operating condition. At step 1006, the controller receives the signal from the sensor. At step 1008, the controller transmits a first message to a remote machine indicating that includes the operating condition. In some embodiments, the remote machine may be the smart workspace system 200 as described herein in conjunction with FIG. 2.

At step 1010, the controller receives a second message from the remote machine to change an operating condition of a device included in the augmented tool, such as disabling the device, enabling the device, or changing the operating speed or temperature of the device. At step 1012, the controller transmits a signal to an actuator to disable, enable, or change the specified operating condition of the device. The method 1000 then terminates.

Figure 11:
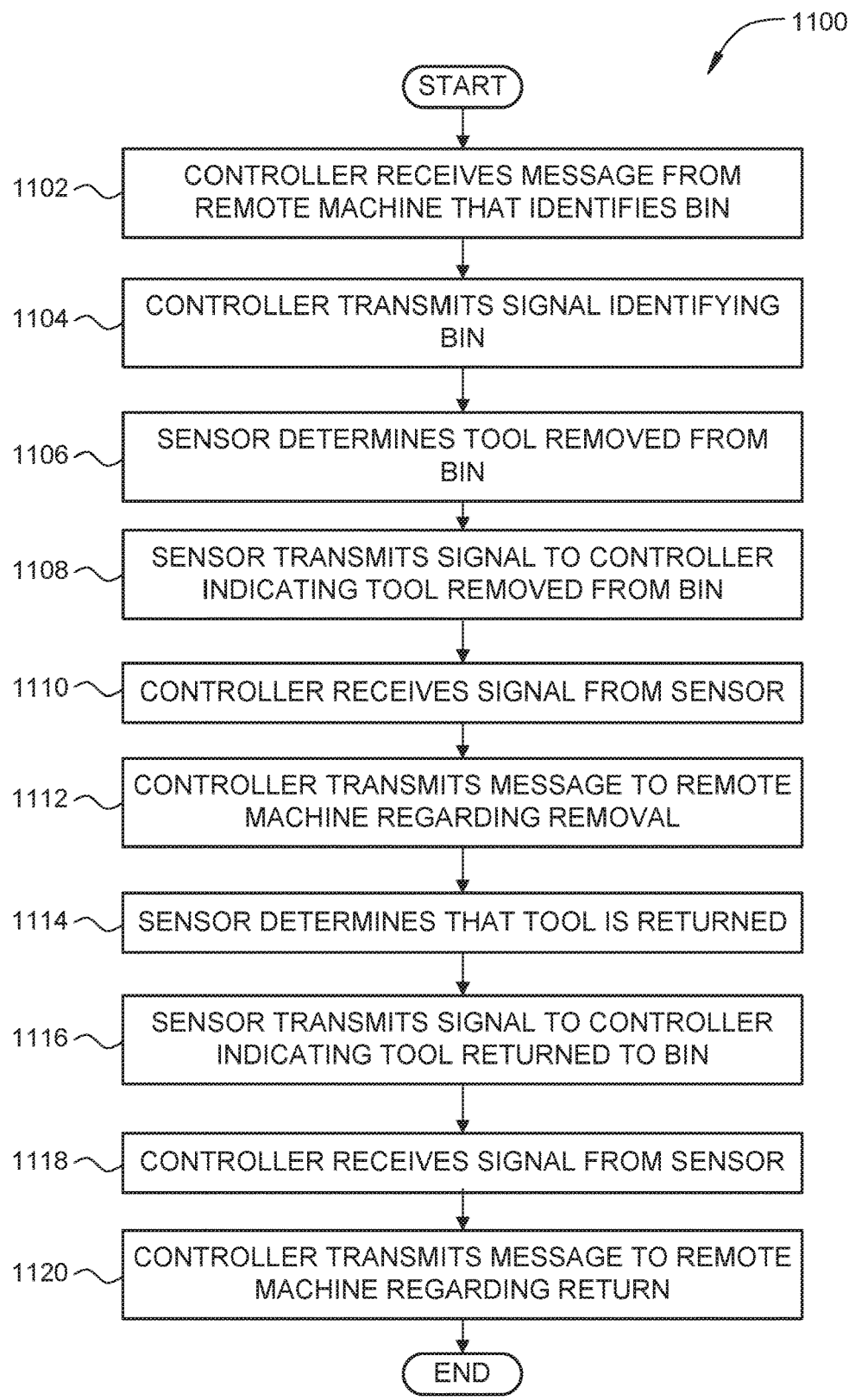
FIG. 11 is flow diagram of method steps for monitoring and controlling the augmented toolkit of FIG. 7, according to various embodiments of the present invention.

FIG. 11 is flow diagram of method steps for monitoring and controlling the augmented toolkit of FIG. 7, according to various embodiments of the present invention. Although the method steps are described in conjunction with the systems of FIGS. 1-7, persons of ordinary skill in the art will understand that any system configured to perform the method steps, in any order, is within the scope of the present invention.

As shown, a method 1100 begins at step 1102, where a controller included in the augmented toolkit receives a first message from a remote machine that identifies a first bin included in a plurality of bins within the augmented toolkit. In some embodiments, the remote machine may be the smart workspace system 200 as described herein in conjunction with FIG. 2. For example, the first bin could include a tool or part that is needed for a particular step of a task. The first message could further specify a quantity of the tool or part that is needed. At step 1104, the controller transmits a first signal to identify a bin. In one example, the controller could send a signal to an indicator, such as an LED, to indicate the first bin. In another example, the controller could send a signal to an actuator that generates any technically feasible visual, audio, or tactile indication of the first bin.

At step 1106, a sensor included in the augmented toolkit determines that a tool or part has been removed from the first bin. In one example, the sensor includes a depth sensor configured to determine when a hand of a user has been placed into the first bin. In another example, the sensor includes a weight sensor configured to determine a weight of the first bin. In yet another example, the sensor includes a radio frequency identification (RFID) sensor configured to determine when a tool associated with the first bin is greater than a threshold distance from the first bin.

At step 1108, the sensor transmits a second signal to the controller indicating that the tool has been removed from the first bin. At step 1110, the controller receives the second signal from the sensor. At step 1112, the controller transmits a second message to the remote machine indicating that the tool has been removed from the first bin. At step 1114, the sensor determines that the tool or part has been returned and placed back into the first bin. At step 1116, the sensor transmits a third signal to the controller indicating that the tool has been returned and placed back into the first bin. At step 1118, the controller receives the third signal from the sensor. At step 1120, the controller transmits a third message to a remote machine indicating that the tool has been returned and placed back into the first bin.

In sum, a smart workspace system provides step-by-step instructions for makers within a public or private makerspace. The smart workspace system provides an overview of the steps for a particular task, details on the current step being performed, and a mechanism to navigate to later and previous steps. The smart workspace system further provides video clips demonstrating the current step, information on how to properly and safely use any tools needed for the current step. The smart workspace system also integrates with augmented safety glasses to provide a warning and disable or change the operation of a tool if the maker is not wearing the augmented safety glasses during the appropriate steps. The smart workspace system also integrates with one or more augmented tools to indicate status of various tools, and control or actuate augmented tools to assist the maker with safe and proper operation of the tools. Finally, the smart workspace system also integrates with an augmented toolkit that identifies needed tools or parts stored in the bins of the augmented toolkit.

At least one advantage of the disclosed techniques is that makers in a public or private makerspace perform steps in a given task safely and efficiently. Makers are reminded to properly use tools and wear safety glasses and are prevented from using tools in a dangerous manner, improving safety and reducing liability in makerspace environments. Another advantage of the disclosed techniques is that makers receive timely guided instructions for each step in a task. As a result, makers may learn new skills more quickly and have a more pleasurable experience when performing DIY tasks in makerspaces.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. An augmented toolkit, comprising:
a toolkit comprising a plurality of bins, wherein each respective bin includes a separate indicator that indicates which bin of the plurality of bins contains one or more requested tools; and
a controller configured to:
receive a first message from a remote machine that conveys that a first quantity of a first requested tool is located in a first bin included in the plurality of bins, wherein the first quantity of the first requested tool comprises two or more separate tools of the same type, and
in response, transmit a first signal to a first separate indicator associated with the first bin to illuminate the first separate indicator,
wherein the first bin further includes a sensor configured to:
detect that the first quantity of the first requested tool has been removed from the first bin, and
in response, transmit a second signal to the controller indicating that the first quantity of the first requested tool has been removed from the first bin.

2. The augmented toolkit of claim 1, wherein the remote machine comprises a smart workspace system configured to communicate with the augmented toolkit to identify one or more tools for performing a plurality of steps associated with a task.

3. The augmented toolkit of claim 1, wherein
the controller is further configured to:
receive the second signal from the sensor, and
in response, transmit a second message to the remote machine indicating that the first quantity of the first requested tool has been removed from the first bin.

4. The augmented toolkit of claim 3, wherein:
the sensor is further configured to:
sense that the first quantity of the first requested tool has been returned to the first bin, and
in response, transmit a third signal to the controller indicating that the first quantity of the first requested tool has been returned to the first bin; and
the controller is further configured to:
receive the third signal from the sensor, and
in response, transmit a third message to the remote machine indicating that the first quantity of the first requested tool has been returned to the first bin.

5. The augmented toolkit of claim 3, wherein:
the sensor is further configured to:
sense that a second tool that replaces the first requested tool has been placed into the first bin, and
in response, transmit a third signal to the controller indicating that the second tool has been placed into the first bin; and
the controller is further configured to:
receive the third signal from the sensor, and
in response, transmit a third message to the remote machine indicating that the second tool has been placed into the first bin.

6. The augmented toolkit of claim 3, wherein the sensor comprises a depth sensor configured to determine when a hand of a user has been placed into the first bin.

7. The augmented toolkit of claim 3, wherein the sensor comprises a weight sensor configured to determine a weight of the first bin.

8. The augmented toolkit of claim 3, wherein the sensor comprises a weight sensor configured to determine a weight of one or more tools within the first bin.

9. The augmented toolkit of claim 3, wherein the sensor comprises a radio frequency identification (RFID) sensor configured to determine when the first requested tool associated with the first bin is greater than a threshold distance from the first bin.

10. A subsystem, comprising:
a plurality of indicators, wherein each separate indicator included in the plurality of indicators is associated with a respective bin included in a plurality of bins, and each separate indicator indicates which bin of the plurality of bins contains one or more requested tools; and a controller configured to:
receive a first message from a remote machine that conveys that a first quantity of a first requested tool is located in a first bin included in the plurality of bins, wherein the first quantity of the first requested tool comprises two or more separate tools of the same type, and in response, transmit a first signal to illuminate a first separate indicator included in the plurality of indicators, wherein the first separate indicator is associated with the first bin, wherein the first bin further includes a sensor configured to:
detect that the first quantity of the first requested tool has been removed from the first bin, and in response, transmit a second signal to the controller indicating that the first quantity of the first requested tool has been removed from the first bin.

11. The subsystem of claim 10, wherein the remote machine comprises a smart workspace system configured to communicate with the controller to identify one or more tools for performing a plurality of steps associated with a task.

12. The subsystem of claim 10, wherein
the controller is further configured to:
receive the second signal from the sensor, and
in response, transmit a second message to the remote machine indicating that the first quantity of the first requested tool has been removed from the first bin.

13. The subsystem of claim 12, wherein:
the sensor is further configured to:
sense that the first quantity of the first requested tool has been returned to the first bin, and
in response, transmit a third signal to the controller indicating that the first quantity of the first requested tool has been returned to the first bin; and the controller is further configured to:
receive the third signal from the sensor, and
in response, transmit a third message to the remote machine indicating that the first quantity of the first requested tool has been returned to the first bin.

14. The subsystem of claim 12, wherein:
the sensor is further configured to:
sense that a second tool that replaces the first requested tool has been placed into the first bin, and
in response, transmit a third signal to the controller indicating that the second tool has been placed into the first bin; and the controller is further configured to:
receive the third signal from the sensor, and
in response, transmit a third message to the remote machine indicating that the second tool has been placed into the first bin.

15. The subsystem of claim 12, wherein the sensor comprises a depth sensor configured to determine when a hand of a user has been placed into the first bin.

16. The subsystem of claim 12, wherein the sensor comprises a weight sensor configured to determine a weight of the first bin.

17. The subsystem of claim 12, wherein the sensor comprises a weight sensor configured to determine a weight of one or more tools within the first bin.

18. The subsystem of claim 12, wherein the sensor comprises a radio frequency identification (RFID) sensor configured to determine when the first requested tool associated with the first bin is greater than a threshold distance from the first bin.

19. The augmented toolkit of claim 1, wherein the remote machine is external to the augmented toolkit.

20. The augmented toolkit of claim 1, wherein, in response to the first quantity of the first requested tool being removed from the first bin, the first separate indicator is extinguished.

* * * * *